United States Patent [19]

Gottlieb

[11] Patent Number: 5,100,663

[45] Date of Patent: * Mar. 31, 1992

[54] TYR-GLY COMPOSITIONS USEFUL IN INCREASING IMMUNE RESPONSE

[75] Inventor: A. Arthur Gottlieb, New Orleans, La.

[73] Assignee: Imreg, Inc., New Orleans, La.

[*] Notice: The portion of the term of this patent subsequent to Mar. 3, 2009 has been disclaimed.

[21] Appl. No.: 469,778

[22] Filed: Jan. 24, 1990

Related U.S. Application Data

[60] Division of Ser. No. 183,905, Apr. 20, 1988, abandoned, and a continuation-in-part of Ser. No. 902,683, Sep. 2, 1986, abandoned, which is a continuation-in-part of Ser. No. 643,724, Aug. 19, 1984, Pat. No. 4,616,079.

[51] Int. Cl.$^5$ .................. A61K 37/02; C07K 5/06; C07K 5/08

[52] U.S. Cl. .................. 424/88; 424/89; 424/92; 514/9; 514/17; 514/18; 514/19; 530/330; 530/331

[58] Field of Search .................. 530/331; 514/18, 19, 514/9, 17; 424/88, 89, 92

[56] References Cited

U.S. PATENT DOCUMENTS

| | | | |
|---|---|---|---|
| 4,127,534 | 11/1978 | Coy et al. | 260/8 |
| 4,468,379 | 8/1984 | Gottlieb | 424/101 |
| 4,537,878 | 8/1985 | Plotnikoff | 514/2 |

OTHER PUBLICATIONS

Bergstroem et al., *Chemical Abstracts*, 1967, 66(3): Abstract No. 10640h, p. 1015.

*Primary Examiner*—Lester L. Lee
*Attorney, Agent, or Firm*—Richard H. Stern

[57] ABSTRACT

Compositions for delaying the progression from AIDS to ARC, and for alleviating symptoms of AIDS and ARC are disclosed together with clinical results of use of such compositions in clinical trials with of actual human patients suffering from these diseases. The compositions are based on a Tyr-Gly amino acid residue sequence. Typical dosage amounts are in the range of femtomoles/kg of body weight.

28 Claims, No Drawings

TYR-GLY COMPOSITIONS USEFUL IN INCREASING IMMUNE RESPONSE

This is a continuation-in-part based on the disclosure contained in U.S. patent application Ser. No. 902,683, filed Sept. 2, 1986, and subsequently abandoned, which priority data is claimed herein. That application was a continuation-in-part based on allowed but then not yet issued U.S. patent application Ser. No. 643,724, which subsequently issued as U.S. Pat. No. 4,616,079, which was filed Aug. 24, 1984, and priority is claimed as to such date. This is a divisional application, resulting from a restriction requirement imposed in U.S. patent application Ser. No. 183,905 (filed Apr. 20, 1988), imposed by Office Action dated Jan. 11, 1989 and now abandoned.

BACKGROUND OF THE INVENTION

1. Field of Invention

This invention concerns cell-mediated immunity and pathological conditions associated with a deficiency in cell-mediated immunity. Such conditions include, in particular, the Acquired Immune Deficiency Syndrome (AIDS), caused by the Human Immunodeficiency virus (HIV), and AIDS-Related Complex (ARC). The invention also concerns other immunodeficient conditions.

A typical manifestation of cell-mediated immunity is the delayed type hypersensitivity ("DH") skin reaction. A DH skin reaction is observed when an appropriate antigen is injected subcutaneously. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings—specifically, perivascular infiltration of leukocytes in the inflamed area. The cells seen at the site of a DH reaction are derived from the peripheral blood leukocyte population.

The mechanisms of cell-mediated immunity are as yet incompletely understood. It is known that the cells which mediate the response are capable of responding in a variety of ways to a challenge from an antigen. These responses include: proliferation of cells bearing specific sensitivity to a given antigen; the induction and multiplication of cells mediating a variety of immune functions, including antibody production; and reactions against foreign cells and tumors.

The present invention relates to the discovery of (1) endogenous amplifiers of the immune system, which are isolated from dialyzed extracts of leukocytes, and synthetic similar products; and (2) compositions containing the amplifiers. These amplifiers profoundly affect the quality and quantity of cell-mediated immunity responses; and are useful in the treatment of AIDS, ARC, and other clinical conditions characterized by inadequate reaction to antigens.

2. Other Background

Earlier Gottlieb Patents: In Gottlieb U.S. Pat. No. 4,468,379, it was disclosed that endogenous materials exist that amplify the speed and magnitude of cell-mediated immune system response. These amplifier materials are distinguished from so-called transfer factors in that amplifiers do not transfer to a subject an immune response to a mitogen or antigen to which the subject has not previously been exposed and is not concurrently exposed, while transfer factors are said to do so. Moreover, amplifiers nonspecifically increase cell-mediated immune system responses to mitogens and antigens to which the subject has previously been or concurrently is exposed, while transfer factors are specific to particular antigens.

The material designed "amplifier 1" in the '379 patent is now known by the inventor to be a mixture of various things. They include what is referred to subsequently in the present patent application as YG-material, what is referred to subsequently in the present patent application as YGG-material, another as-yet undefined amplifier, various amino acid products, and other materials. The foregoing materials occurred in amplifier 1 in varying proportions, depending on the identity of the blood sample from which the sample of amplifier 1 was derived; the reason for that is that the content of a human blood sample varies from donor to donor and even for the same donor from time to time, depending on the state of the immune system of the donor. The fact that the content of amplifier 1 varied from sample to sample adversely affected the repeatability of experiments directed toward establishing the immunological activity of amplifier 1. That in turn adversely affected ability to establish product identity, standard dosages, assays, and the like for amplifier 1.

It was suggested in Gottlieb U.S. Pat. No. 4,616,079 (from which the parent of this application was divided and of which said application was a continuation-in-part) that amplifiers appear to act on T-helper cells (T4 cells) in a way that causes them to produce chemical mediators (lymphokines) whose effect is to increase the speed and/or magnitude of cell-mediated immune system response to antigens and other means of activating a cell-mediated immune system response. (The term "recall antigen," as used hereinafter, refers to an antigen to which a subject has previously been exposed.) Indicia of this response include DH reaction to recall antigens, production of IL-2 and gamma interferon, and potentiation of cytotoxic cells.

It is known that various diseases and pathological conditions, such as Acquired Immune Deficiency Syndrome (AIDS) and AIDS-Related Complex (ARC), as well as chemotherapy, radiation and ageing, depress the immune system response. As a result, there is increased susceptibility to opportunistic infections, malignancies, and other pathological conditions that a normal immune system would have confronted. Frequently (and for some conditions, invariably), the result is death. Administration of amplifiers provides a means of improving cell-mediated immune system responsiveness, where the cell-mediated immune system remains sufficiently intact for it to respond to such administration.

Earlier Gottlieb patents describe means of extracting amplifier materials from human leukocyte dialysates by reverse-phase HPLC processes. However, until recently the inventor did not have sufficiently detailed information about the molecular structure of the constituents of such purified dialysate fractions to permit identification of the structures of their immunologically active components, in large part because a way had not yet been discovered to purify the dialysates sufficiently to permit necessary analysis. In an application filed during the pendency of the parent applications of the instant application, and now issued as Gottlieb U.S. Pat. No. 4,699,898, as well as in other related patent applications of the inventor, the inventor disclosed his discovery of peptide products containing Tyr-Gly and Tyr-Gly-Gly amino acid residue sequences, that are immunologically active components in the partially purified dialysate fractions previously described in earlier Gottlieb patents, such as Gottlieb U.S. Pat. No. 4,616,079 (from which this application is descended as a continuation-in-part).

The earlier Gottlieb patents may also be consulted for other general background information on amplifiers and their use. In this regard, mention should also be made of Gottlieb EPO pat. app. pub. no. 0173889 (12.03.86), which is based on both Gottlieb U.S. Pat. No. 4,699,898 and the parent application of the instant application.

Coy: Coy U.S. Pat. No. 4,127,534 describes tripeptides of the form Tyr-X-Gly, where X is a D-aminoacid. Coy asserts that these products have analgesic and related utility, as indicated by rat tail flick or other tests; accordingly, they may be used as substitutes for such medications as aspirin and sedatives. Coy claims pharmaceutical compositions that contain a "therapeutically effective amount" of Tyr-X-Gly, including Tyr-D-Ala-Gly. Coy asserts in the body of his specification that a therapeutically effective amount of the product for purposes of the disclosed utility is from 0.001 mg per kg of bodyweight to 100 mg per kg of bodyweight, administrated daily. (Extrapolated to an 80 kg person, this amounts to a daily dose of approximately 0.1 mg to 10 g; 0.1 mg is equivalent to approximately 300 nanomoles, and 10 g is equivalent to approximately 0.03 moles.) It should be noted that the relevant language of Coy's specification is in the present tense, indicating use of prophetic examples. (No therapeutic examples are provided in the specification, and no statements about utility or dosage are made in the past tense.)

Coy does not assert any immunological use of the products. Coy does not describe any of the D-aminoacid group as a means of preventing cleavage of the Tyr-Gly bond by endogenous enzymes. Coy does not describe any utility for doses of less than the aforesaid minimum daily amounts (0.001 mg/kg, 0.1 mg, and 300 nM).

Plotnikoff: Plotnikoff U.S. Pat. No. 4,537,878 discloses and claims the use of endogenous endorphins and enkephalins to stimulate the immune system. The dosage amounts actually used in vivo (Plotnikoff's Examples VIII to XI) were from 1 microgram (ug) per kg to 50 ug/kg, single i.v. dose. Elsewhere, however, Plotnikoff refers to a therapeutic dose of from 1 ug/kg to 30 mg/kg, and to a preferable dosage rate of from 0.01 fg/kg to 250 ug/kg. No explanation is given for the inconsistencies, and no data in the specification indicates a reason why these latter dosage rates were mentioned or claimed. (They do not appear in examples or similar data.)

The molecular species whose use Plotnikoff discloses are the endogenous enkephalin pentapeptides Tyr-Gly-Gly-Phe-Leu and Tyr-Gly-Gly-Phe-Met, and longer endorphin polypeptide extensions thereof (extended from the C-terminal end). Plotnikoff does not disclose use of any nonendogenous peptides, nor anything concerning use of dipeptides, tripeptides, or tetrapeptides. Plotnikoff does not indicate that Tyr-Gly or Tyr-Gly-Gly have any immunological or other utility. Plotnikoff does not show that any products have utility in treating AIDS or ARC.

Schwartz: Schwartz et al., *Biological inactivation of enkephalins and the role of enkephalin-dipeptidyl-carboxypeptides ("enkephalinase") as neuropeptidase,* 29 Enkephalin Metabolism 1715 (1981), extensively reviews work that has been done in the field of enzymatic breakdown of enkephalins. Schwartz summarizes the paper as follows:

In this review it will be shown that enkephalins are rapidly hydrolyzed in vivo and that several peptidase activities have been identified which are able to cleave these molecules to give various *biologically-inactive fragments.* (Emphasis added.)

Schwartz et al. and the work summarized in the review teach that various endogenous enzymes cleave (hydrolyze) the Gly-Phe, Gly-Gly, and Tyr-Gly bonds of endogenous mammalian polypeptides, such as Leu-enkephalin (Tyr-Gly-Gly-Phe-Leu) and Met-enkephalin (Tyr-Gly-Gly-Phe-Met), into what Schwartz alleges are "biologically inactive fragments." Such fragments include what Schwartz refers to as Tyr-Gly, which in context apparently means a dipeptide containing Tyr and Gly amino acid residues, in that order. But Schwartz does not indicate what side chains or other groups, if any, are attached to the amino acid residues or what specific molecular structure is present in the Tyr-Gly product.

Schwartz and the work summarized in the review also disclose various means of inhibiting such enzymatic cleavage, including N-methylation of the Tyr residue; esterification, amidification, and alcoholation of the C-terminal carboxyl; insertion of a D-aminoacid residue (such as D-Ala) into the chain near the C-terminal end; and mixture with bacitracin, puromycin, bestatin, amastatin, or thiorphan. (It is also known in pharmaceutical art, although not discussed in Schwartz, to bind or complex an enzyme-inhibiting agent to a therapeutically active molecule, so that the agent will preferentially bind to the active site on the enzyme that is to be inhibited, thereby preempting that site and thus keeping the enzyme from hydrolyzing the molecule to be protected. This is exemplified by the use of the product sulbactam, a beta-lactamase inhibitor used to protect ampicillin from beta-lactamase; thus, UNA-SYN ™ (Pfizer) is a mixture of sulbactam and ampicillin, while sultamicillin is ampicillin complexed or otherwise linked with sulbactam via an ester. It is also known, for example in the case of the synthetic penicillins, to introduce a large group (such as methyl) at a location on a therapeutically active molecule where there would otherwise be a space providing a site for enzyme attachment, which results in hydrolysis. The result of occupying such a space is to inhibit enzymatic degradation of the molecule thus protected.)

The Schwartz paper does not mention any immunological activity or other utility of the allegedly useless and biologically inactive fragments resulting from enzymatic action on enkephalins.

Delivery of drug via hydrolysis: It is known that a therapeutically active molecule may be delivered by administering to a patient a different molecule that hydrolyzes, as a result of the action of endogenous enzymes, to fractions that include the desired therapeutically active molecule. Perhaps hetacillin is the best known example. Hetacillin breaks down in the human body to ampicillin. A legal controversy ensued internationally, following the introduction of hetacillin, over whether the manufacture, use, and sale of hetacillin infringed patents on ampicillin.

Commercial Tyr-Gly: Tyr-Gly is sold as a chemical reagent (L-tyrosylglycine) by Sigma Chemical Co., St. Louis, Mo., among others. Tyr-Gly is not sold in U.S.P.

grade, and it is illegal under applicable laws to sell Tyr-Gly for use as a pharmaceutical. Commercial grade Tyr-Gly is not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations. To the extent of the inventor's knowledge, no pharmaceutical preparations of this product are or have been available.

Commercial Tyr-Gly-Gly: Tyr-Gly-Gly is sold as a chemical reagent (L-tyrosylglycylglycine) by Sigma Chemical Co., St. Louis, Mo., among others. Tyr-Gly-Gly is not sold in U.S.P. grade, and it is illegal under applicable laws to sell Tyr-Gly-Gly for use as a pharmaceutical. Commercial grade Tyr-Gly-Gly is not considered free of pyrogens, endotoxin, and other pharmaceutically unacceptable constituents. The presence of such pyrogens, endotoxin, and other pharmaceutically unacceptable constituents makes a product unacceptable for use as a drug, as that term is defined by federal statute, both under generally recognized medical principles and under FDA regulations. To the extent of the inventor's knowledge, no pharmaceutical preparations of this product are or have been available.

SPECIAL TERMINOLOGY

YG means Tyr-Gly (also known as L-tyrosylglycine). YGG means Tyr-Gly-Gly (also known as L-tyrosylglycylglycine).

YG-material means a member of a group consisting of a set of molecular species wherein each molecule contains a Tyr-Gly amino acid residue sequence, and no other amino acid residues. The molecule may be in the form of a simple Tyr-Gly sequence, or the molecule may be methylated, amidified, esterified, acetylated, etc. YG-material does not include tripeptides or higher polypeptides. However, two YG-materials (e.g., two molecules of Tyr-Gly) may be complexed together in the form: (Tyr-Gly)Zn++(Tyr-Gly), or they may be dimerized as in the form:

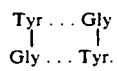

Such a complex or dimer is not considered a tetrapeptide, but merely two dipeptides complexed together or dimerized.

YGG-material means a member of a group consisting of a set of molecular species wherein each molecule contains a Tyr-Gly-Gly amino acid residue sequence, and no other amino acid residues. The molecule may be in the form of a simple Tyr-Gly-Gly sequence, or the molecule may be methylated, amidified, esterified, acetylated, etc. YGG-material does not include dipeptides, tetrapeptides, or higher polypeptides. However, two YGG-materials (e.g., two molecules of Tyr-Gly-Gly), or YG-material and YGG-material, may be complexed together or dimerized. Such a complex or dimer is not considered a pentapeptide or hexapeptide.

Inhibited YG-material means YG-material that has been mixed, complexed, bound, linked, or otherwise combined with a means for inhibiting cleavage of the Tyr-Gly bond of the molecule by endogenous enzymes; however, the material must still contain a Tyr-Gly amino acid residue sequence and no other amino acid residue sequence. Puromycin and bacitracin are examples of inhibitors that may be mixed with YG-material. It is also known to N-methylate the Tyr residue to inhibit enzymatic action. It is also known to esterify or amidify the C-terminal carboxyl group to inhibit enzymatic cleavage. The products of such expedients are hereinafter termed inhibited YG-material. Inhibited YG-material does not include expanded YG-material, as defined below; the two terms are mutually exclusive. Also, the term "inhibited YG-material" falls within the scope of the term "YG-material."

Expanded YG-material means a molecule of the form Tyr-X-Gly, where X is a D-aminoacid, such as D-Ala. The term includes amides, esters, salts, etc., as in the case of YG-material. It is known that the insertion of a D-aminoacid into Tyr-Gly tends to inhibit cleavage of the Tyr-Gly bond by endogenous enzymes. The terms YG-material and expanded YG-material are mutually exclusive, since the former is a dipeptide and the latter is a tripeptide; also the former has a Tyr-Gly bond and the latter does not.

Endogenous YG-material means YG-material produced within the body. Endogenous YGG-material means YGG-material produced within the body.

Extraneous-peptide amino acid residue sequences means any and all amino acid residue sequences except Tyr-Gly and Tyr-Gly-Gly. As used herein, "sequence" refers to a plurality of residues, and the terms excludes a molecule with only a single amino acid residue, such as glycine.

The abbreviation u, n, p, and f refer, respectively, to micro, nano, pico, and femto. The abbreviation M means moles or Molar, as the context indicates; thus, fM may mean femtomoles or femtoMolar, depending on context.

The term "fg/kg," used in the claims in connection with a dosage amount for a person, means femtograms of dosage material per kilogram of the person's bodyweight. Similarly, "moles/kg" means moles or dosage material per kilogram of the person's bodyweight; "fM/kg" means femtomoles per kilogram of the person's bodyweight.

The term "packaged," used with reference to a pharmaceutical composition, means placed into a vial, capsule, tablet, suppository, prefilled syringe, or other form adapted for containing pharmaceutical products for administration to persons or for veterinary use. As used here, "packaged" implies sterile and fit for administration to persons or for veterinary use. It also implies freedom from pyrogens, endotoxin, and similar medically unacceptable contaminants.

SUMMARY OF THE PRESENT INVENTION

The inventor has discovered that administration to AIDS and ARC patients of endogenous materials containing the amino acid residue sequence Tyr-Gly (YG) can alleviate certain symptoms of AIDS and ARC, can reverse certain pathological effects associated with AIDS and ARC, and appears to improve the clinical condition of some AIDS and ARC patients. Such treatment does not cure AIDS and ARC, but it is therapeutically useful in slowing the normal progression of AIDS and ARC. In particular, the treatment significantly delays the normal progression to AIDS that occurs in ARC patients. It also alleviates some symptoms of AOIDS and ARC, and is useful in treating candidiasis.

The inventor has also discovered more general immunological utility for the foregoing endogenous materials and related synthetic materials. The materials of the invention are amplifiers of the immune system (as that term is used in Gottlieb U.S. Pat. No. 4,616,079). Thus they may be used for the therapeutic purposes described in the above-cited Gottlieb patents.

Generally speaking, the endogenous products of this invention are the reult of the inventor's discovery of processes leading to highly purified forms of amplifier materials, while the synthetic products are products whose potential immunological utility was suggested to the inventor by his discovery of the molecular structure of immunologically active constituents of the foregoing endogenous products of this invention. The instant products are thus more free of extraneous material than any earlier amplifier products were, and the synthetic such products have the considerable advantage that they are not derived from human body components, which may (correctly or incorrectly) be thought to harbor viruses and other pathogens.

Further, the elimination of extraneous material and the fractionation of mixtures of molecular species into the constituent species has resulted in achieving greater potency and repeatability in the resulting products than was possessed by the initial materials.

DETAILED DESCRIPTION OF THE PREFERRED EMBODIMENTS

Section I of this specification describes HPLC processes for purification of endogenous amplifier materials derived from human leukocyte dialysates. Section II describes human biological assays of the immunological activity of such materials. Section III describes human therapeutic use of such materials, including treatment of over 30 AIDS and ARC patients. Section IV describes in vivo and in vitro tests of synthetic amplifiers whose molecular structure is based on that of the endogenous amplifier materials described in the preceding sections. Section V describes some other applications.

I. Reverse Phase Liquid Chromatography Processes

Processes are now described by which endogenous amplifier materials are extracted from human leukocyte dialysates. The procedures and reagents used herein were chosen to provide sterile and non-toxic products for human treatment. The HPLC equipment used is that described in Gottlieb U.S. Pat. No. 4,616,079 (from which this application descends as a continuation-in-part), cols. 5–6.

EXAMPLE 1

Extraction of Beta and Zeta

Leukocyte pellets were prepared in accordance with Example 1 of Gottlieb U.S. Pat. No. 4,616,079 and set aside.

An aqueous potassium phosphate solution was prepared by adding 5M KOH aqueous solution dropwise to 0.02M reagent grade phosphoric acid aqueous solution until the pH of the solution was adjusted to pH 5.0. The solution was delivered to a Perkin-Elmer HPLC machine, along with HPLC grade acetonitrile. The machine was programmed to deliver the following input solvent gradients: (1) 10 minutes of 0.1% concentration of acetonitrile in phosphate solution, constant gradient; and (2) 45 minutes of 0.1% to 10.0%, linear gradient. The flow rate wa set at 1 ml/min.

Then, the leukocyte pellets were reconstituted and 5-10 mg of the material was loaded into a "mu Bondapak" O.S. column. HPLC was commenced.

As effluent was collected, the ultraviolet absorption of the effluent was scanned with the machine's ultraviolet detector (210 nm, full scale=0.32 units). A plot of the absorption data of this process is shown in FIG. 1 of Gottlieb U.S. Pat. No. 4,616,079. Apparent solvent concentrations, retention times, and ultraviolet absorption were recorded. The results of the run are summarized below:

Alpha. A distinct double ultraviolet absorption peak was observed at retention tim 12-14 minutes (approximately 0.5 to 0.9% acetonitrile concentration as observed on the machine's display and approximately 0.1 to 0.2% estimated actual concentration). The material accompanying this peak is designated herein as Alpha. It has no known immunological activity. But its elution serves as an indication ("marker") that material designated herein as Beta, which has been discovered to have amplifier activity, is about to elute.

Beta. Beta eluted approximately 3 minutes later, between approximately 15 and 20 minutes retention time. It was accompanied by a sharp, single ultraviolet absorption peak (hereinafter referred to as the Beta peak) reaching full scale. Displayed solvent concentration was 1.2 to 2.2%; estimated solvent concentration was 0.4 to 1.5%.

Frequently, in runs of this process, the material at the front edge of the Beta peak contained a material hereinafter described as Beta 1.12 and identified as endogenous YGG-material. Sometimes, such material appeared as a shoulder on the Beta peak. (As described below, Beta material can be fractionated further.)

Gamma. Immediately after Beta, at retention time between approximately 17 and 22 minutes, material designated herein as Gamma eluted. The Gamma material was characterized by either a distinct broad peak of ultraviolet absorption or as a shoulder on the absorption indication at the end of the elution of Beta. Gamma is without known immunological activity.

Delta. A group of peaks were then observed in the retention time range of from 23 to 36 minutes. The first of these peaks (a rather low one, less than 30 or 40% of full scale) corresponded to (i.e., occurred with the elution of) biological material designated herein as Delta, which has been discovered to have amplifier activity. Delta eluted in the retention time range of approximately 26-28 minutes. Solvent concentration indicated on the visual display of the machine was from 3.5 to 4.0%, while estimated actual solvent concentration was 2.8 to 3.3%. Delta did not maintain a well-fixed location in this process, and sometimes either did not come off the column at all or was buried in the next material (Epsilon).

Epsilon. The next large absorption peak in the group was approximately 20% (or much more) of full scale, occurred about a minute later at retention time 27-30 minutes, and was a broad single peak or a doublet; the peak accompanied material designated herein as Epsilon. Epsilon is without known immunological activity.

Zeta. The absorption peak immediately following, approximately 2 minutes later, at retention time about 29-32 minutes, is designated herein as Zeta. Zeta has been discovered to have amplifier activity. As indicated below, Zeta can by a further process be separated into two moieties, Zeta-1 and Zeta-2, the second of which is has been discovered to contain the entire amplifier activity of thus material.

Other materials, not discussed herein, but discussed in Gottlieb U.S. Pat. No. 4,161,079, eluted thereafter in this process.

The materials of Example 1 are contaminated with phosphate ions, are imperfectly purified from extraneous material (material having no known useful immunological activity), and are considered unsuitable for administration to human subjects. A further HPLC procedure with a different solvent system has been discovered to remove phosphate and extraneous material. The resulting material appears to be considerably more free of extraneous material and was considered suitable for administration to human subjects (as discussed below).

EXAMPLE 2

Beta-1.0 Process

The material of preceding Example 1 was further purified and separated by HPLC on the analytic column. First, a 0.1% (v/v) aqueous trifluoroacetic acid (Mallinckrodt, Inc., Paris, Ky.) solution was prepared, and the pH of the solution was adjusted to pH 2.5 by the dropwise solution of sufficient 5M KOH aqueous solution. The solution was delivered to the Perkin Elmer machine, along with HPLC grade acetonitrile.

The machine was programmed for a 45 minute linear gradient of 0.1% to 45% concentration of acetonitrile in the trifluoracetic acid solution. (A 25-minute run to 25% is acceptable, but 45 minutes to 45% is more conservative). The flow rate was set at 1 ml/min.

Beta fractions from approximately 4 procedures of Example 1 were pooled and loaded s starter material into a "mu Bondapak" brand of O.S. column; and HPLC was commenced. The effluent were scanned with the ultraviolet absorption detector, as in the preceding example. Full scale was set at 1.28 absorption units.

Contaminating Gamma material eluted at 8-11 minutes and wad discarded. Displayed solvent concentration range was 8-11%; estimated actual solvent concentration was 4.8-7.8%. The absorption peak associated with Gamma was approximately 30-40% of full scale.

Material hereinafter designated as Beta-1.0 eluted at 15-18 minutes. Displayed solvent concentration range was 15-18%; estimated actual solvent concentration was 11.8-14.8%. The absorption peak was at least full scale and was quite sharp.

Analysis of Beta-1.0 indicates the presence of a mixture of molecular species. Two have been found to have intrinsic amplifier activity and are further discussed hereinafter. These two are a dipeptide material consisting essentially of a YG sequence, and a tripeptide material consisting essentially of a YGG sequence. The relative amounts of YG-material and YGG-material vary from sample to sample, as is to be expected with human-derived immunologically active products, but the average ratio of YG-material:YGG-material is between 16:1 and 20:1. In addition, a third intrinsically active amplifier has been found present, which consists of a nonpeptide, and is present in approximately the same relative amount as YGG-material. In addition, dried Beta-1.0 contains approximately 90% phenylalanine plus small amounts (less than 5% (w/w)) of other materials, notably Phe-Ser, Gly-Gly, and Gly-Glu; all of these materials were tested and found to lack intrinsic amplifier activity. Extensive clinical work with Beta-1.0 is described hereinafter. The terms "Beta-1.0" and "IMREG-1" are interchangeable.

EXAMPLE 3

Zeta-2 Process

The procedure of Example 2 was repeated, except that the starter material used was Zeta material of Example 1.

Zeta fractionated into two moieties—hereinafter designated Zeta-1 and Zeta-2. The first is without known immunological activity. The second appears to have all of the amplifier activity of Zeta.

Zeta-1 eluted at approximately 11-14 minutes (displayed solvent concentration range, 11-14%; estimated actual solvent concentration range, 7.8-10.8%). Zeta-2 eluted at approximately 15-19 minutes (displayed solvent concentration range, 15-19%; estimated actual solvent concentration range, 11.8-15.8%). Their absorption peaks were quite sharp and were separated by an average of 2-3 minutes.

Mass spectrometer analysis of Zeta-2 did not indicate any peptide components. Although not conclusive, they suggested that Zeta-2 consists essentially of one or more molecules of the prostaglandin family, with blocked hydroxyl groups. It is believed that Zeta-2 has a M.W. of approximately 250 to 300. It is possible (but not ascertained) that Zeta and Zeta-2 are present in the mixture of products known as "amplifier 1," along with Beta-1.0, thereby contributing to the immunological activity of amplifier-1. For the present purpose, it is scientifically supported only to characterize Zeta-2 as follows: One or more small, non-peptide molecules of M.W. approximately 250 to 300; eluted from an HPLC octadecylsilane column with a solvent system of acetonitrile in aqueous trifluoroacetic acid solution in the portion of the gradient where the acetonitrile concentration of the effluent is from 11.8% to 15.8%; characterized further by a sharp UV absorption peak, separate from and distinguishing it from Zeta-1, which is associated with an earlier sharp peak (see FIG. 2A, U.S. Pat. No. 4,616,079.)

Delta has not been recovered by use of this procedure; Delta may be destroyed by the trifluoroacetic acid.

Further refinements have been developed that further purify these products, remove additional extraneous material, and make the materials some suitable for human administration. The Beta material of Example 1 has been further fractionated and refined by these techniques, and the resulting products have become sufficiently purified to permit amino acid analysis thereof. That in turn has led to a determination of the probable molecular structure of the fractions in question.

EXAMPLE 4

Ethanol/Beta-1.1 Process

The Beta material developed from the pH 5 phosphate gradient of Example 1 was dried in a vacuum evaporator without heat. The material was reconstituted in 0.1% trifluoroacetic acid. A Perkin-Elmer preparative column was used for HPLC; a 3.5 cm × 28 cm column was packed with octadecylsilane, and the reconstituted material was introduced. A flow rate of 6.0 ml/min was set. The machine was programmed to deliver a ethanol-in-water linear input gradient, starting at 0% ethanol and reaching 50% at 30 minutes.

Absorbance was monitored at 254 mm, 0.1 Absorbance Units=Full Scale. Three major peaks were observed, which respectively eluted at 10.4–10.6 min, 14.0–16.0 min, and 18.0–19.0 min. The biological activity was assayed and found to reside almost entirely in the material associated with the middle peak, which is designated herein as Beta-1.1. The last peak was found to be associated with material that was mainly phenylalanine and contained approximately 90% of the starting material used. The first peak was lower than the second and third, in terms of absorbance units, and is believed to be an artifact of the system associated with the ethanol solvent or due to elution of salts. The second and third peaks varied in relative height from preparation to preparation.

Based on refractive index measurements, the ethanol concentration of the effluent of the second peak was found to be from approximately 0.1% to approximately 0.4%.

An amino acid assay of the material associated with the Beta-1.1 peak was made, with the following normalized results:

| | |
|---|---|
| Asx | 2 |
| Thr | 1 |
| Ser | 1 |
| Glx | 1 |
| Pro | 2 |
| Gly | 4 |
| Ala | 2 |
| Val | 1 |
| Ile | 1 |
| Tyr | 1 |
| Lys | 3 |
| His | 1 |
| Arg | 1 |
| | 23 |

For a number of reasons, the inventor did not believe that the Beta-1.1 endogenous amplifier material was a polypeptide with 23 peptide groups, or a mixture of 3 octapeptides, or the like. The inventor determined that still further purification of the materials of the foregoing process would be desirable, to ascertain whether one or more immunologically active materials were present in which there were substantially fewer peptide groups.

To date, this has resulted in the extraction of two materials having considerably greater amplifier activity than Beta-1.0 or Beta-1.1: a dipeptide material and a tripeptide material. An acetonitrile HPLC process was developed that permitted such a result and it is described in the following example. We have obtained best results with a Dupont brand of resin column (known as ZORBAX TM), which comes packed with a Dupont material containing octadecylsilane groups chemically bonded to silica particles. All references to HPLC resin columns hereafter should be understood to refer to the foregoing type of Dupont material.

EXAMPLE 5

Purification of Beta-1.1 to Beta-1.11, Beta-1.12, and Beta-1.13

The Beta-1.1 material of Example 4 was injected into an ODS HPLC column (Dupont), 1 ml/min flow rate, 25° C. The solvent system was 100% acetonitrile (CH$_3$CN), HPLC Grade, and 0.05% trifluoroacetic acid aqueous solution, HPLC Grade, pH 2.5. The following solvent input linear gradients were used: (1) for 15 minutes, from 0–6% acetonitrile; (2) for 30 minutes, from 6–40% acetonitrile.

A fraction of interest, hereinafter designated as Beta-1.11, eluted at approximately 23.8 to 24.8 min, for a new column. It was associated with a sharp, narrow peak of UV absorption at 210 nm; this peak is approximately the fourth absorption peak observed (some variability existing). The material was lyophilized and reconstituted in normal saline, and set aside for further use. As shown below, Beta-1.11 contains endogenous YG-material.

Another fraction of interest, eluted from this material on this column, but somewhat irregularly. When it eluted, the retention time was approximately 22.8–23.2 min. It was associated with a distinct peak of ultraviolet absorption at 210 nm, a third peak which is just before the peak associated with Beta-1.11, and which often partially overlaps with the third peak. The material was lyophilized and reconstituted in normal saline, and set aside for further use. As shown below, this material, hereinafter referred to as Beta-1.12, contains endogenous YGG-material.

A fifth UV peak is associated with material having no intrinsic activity. A sixth UV peak is associated with phenylalanine. A seventh peak, discussed below, is associated with active material of as-yet undefined structure.

Other moieties found present in effluents of this process were Gly-Gly, Ser-Phe, and Ala, along with possibly other amino acid residues as well. None of these other moieties appeared to possess immunological activity, as assayed by DH test.

To avoid confusion between the first two moieties of interest, particularly in the case of aged columns, it has been found advantageous to run purified commercial YGG through the column as a marker. Such YGG elutes reproducibly 0.8 to 1.2 min before Beta-1.11 (approximately the same zone as Beta-1.12).

Finally, another fraction of interest may be eluted from the material on this column, at a retention time of approximately 31.5 min. It was associated with a sharp peak of UV absorption at 210 nm, a seventh peak considerably after the third and fourth peaks associated with Beta-1.11 and Beta-1.12. As discussed below, this material, hereinafter referred to as Beta-1.13, is immunologically active.

THE ENDOGENOUS AMPLIFIERS OF THIS INVENTION

The Beta-1.11 material was then subjected to amino acid sequencing procedures. Using standard techniques, such as those described in Example 4 of Gottlieb U.S. Pat. No. 4,699,898, it was determined that Beta-1.11 contains Tyr and Gly, which come off in that order, in approximately equal proportions. This indicated the presence of a YG-material. (A protein/peptide sequencer automatically removed one amino acid at a time from the N-terminal end of a protein or peptide for determination of amino acid sequence.) It was thus ascertained that Beta-1.11 is endogenous YG-material. (Those two terms are interchangeable for the purpose of this specification.)

Some YGG-material as also detected in this material, which has been found to be immunologically active, as is discussed below. Small amounts of Ile and Lye were also detected. Those may be artifacts of the procedure, or may indicate small amounts of Ile/Lye components in a molecule or molecules present in relatively low concentrations in the product (such as, hypothetically, Tyr-Ile-Lys, Tyr-Gly-Lys, Tyr-Gly-Gly-Ile). The inventor presently believes that the Ile/Lys material is simply an artifact or a nonsignificant component.

The Beta-1.12 material was also subjected to amino acid sequencing procedures and was identified as containing a Tyr-Gly-Gly amino acid residue sequence, indicating the presence of a YGG-material. It was thus ascertained that Beta-1.12 is endogenous YGG-material. (Those two terms are interchangeable for the purposes of this specification.)

It has not been ascertained whether iosmeric forms are present, whether the YG- and YGG-materials of Beta-1.11 and 1.12 have other groups bound to them (e.g., methyl, acetyl, amide), or whether complexes with metal ions (such as, possibly, $Zn++$, $Ca++$, $Fe++$, $Mn++$, or $Mg++$) are present, and if so whether the different forms, if any, possess different immunological activity. While it would be desirable to ascertain this, the present state of the art makes it difficult or impossible to do so.

As indicated below, certain immunological assay data suggests that Beta-1.11 and Beta-1.12 are in some way different from chemically manufactured (synthetic) YG and YGG, respectively, because the endogenous products extracted from human leukocyte material appear to have greater immunological activity than the purified synthetic peptide chemicals. (The purified chemicals do not have methyl, acetyl, etc. substitutions and they are not complexed with $Zn++$ or other ions. But as indicated above the endogenous products may have such structural variations.)

There is reason to infer that the naturally occurring Beta-1.11 and 1.12 amplifier products are present in the human or animal body in the form of a complex of $(X)M++(Y)$, where $(X)$ and $(Y)$ are each selected from the group consisting of Tyr-Gly, Tyr-Gly-Gly, or a derivative thereof, and where $M++$ is $Zn++$ or another divalent metallic ion such as $Ca++$, $Fe++$, $Mn++$, or $Mg++$. There is a negative site on the Tyr group that may bind to the $M++$ ion; there is also a C-terminal negative site on the last Gly that may so bind. There may well also be a mixture of such complexes.

Some work was done on the ratio of Tyr-Gly and Tyr-Gly-Gly components in human materials, by radioiodinating the Tyr groups and then separating the Tyr-Gly and Tyr-Gly-Gly moieties by gel electrophoresis in order to compare the respective amounts of the moieties. If there were only a $(Tyr-Gly)M++(Tyr-Gly-Gly)$ complex, one could anticipate a constant 1:1 ratio of YG and YGG. But that does not occur; instead, the proportions observed varied from sample to sample, but averaged YG:YGG = 18:1. Possibly, there are several different materials or complexes—such as $(Tyr-Gly)M++(Tyr-Gly)$, $(Tyr-Gly)M++(Tyr-Gly-Gly)$, and $(Tyr-Gly-Gly)M++(Tyr-Gly-Gly)$—in varying proportions, depending on as yet unidentified physiological parameters.

From the foregoing amino acid sequencing data, in conjunction with biological assay data described below, the inventor concludes as follows: Two biologically significant components of the Beta-1.1 material described above may be further characterized as containing the amino acids Tyr and Gly, in a 1:1 or 1:2 ratio, and as not containing substantial amounts of any other amino acid. The YG- and YGG-materials present in the Beta materials may exist as a mixture of variable proportions; either or both molecules may be complexed with metal ions (such as $Zn++$, $Ca++$, $Fe++$, $Mn++$, or $Mg++$); both may be complexed together, with the possible addition of metal ions. The materials eliminated from the final materials, such as Phe (approximately 90% of Beta-1.0), Phe-Ser, Gly-Gly, and Gly-Gly, do not possess intrinsic immunological activity, but they may endogenously co-act with the YG- and YGG-materials to enhance their stability or immunological activity.

The foregoing series of processes began with a leukocyte dialysate containing an extract from approximately $10^{10}$ leukocytes. This yielded approximately 84 ug of Beta-1.0 or, alternatively, somewhat less Beta-1.1. The Beta-1.1 in turn yielded approximately 168 ng of endogenous YG-material and 3 ng of endogenous YGG-material each. A quantity of 1 to 5 pg of endogenous YG-material, which is approximately one clinical dosage unit, as discussed below, is thus derived from approximately $1-2\times 10^5$ leukocytes. (However, the same starting material also yields about 10% of that amount of endogenous YGG-material.)

The inventor has also discovered that the existence of a third immunologically active component in Beta-1.1, designated herein as Beta-1.13. This component elutes from the system of Example 5, as stated above, at approximately 31.5 min, for a new column. It is characterized by a sharp, narrow peak of UV absorption at 210 nm; this peak is approximately the seventh absorption peak observed in the procedure of Example 5. Beta-1.13 is believed to be a ring product, not a peptide, having a M.W. of approximately 250 to 300. Beta-1.13 has occurred in leukocyte dialysate samples in what appears to be approximately the same amount as did Beta-1.12 (i.e., 5% to 10% as much as Beta-1.11). The inventor believes that Beta-1.13 is a single molecular species, not a mixture of different molecular species, but that face has not as yet been proved.

II. Human Biological Assay Data

Additional biological assay methods have been developed, which were not described in Gottlieb U.S. Pat. No. 4,478,379, Gottlieb U.S. Pat. No. 4,616,079 (of which this application is a continuation), or Gottlieb U.S. Pat. No. 4,699,898. The following additional assay methods have now been found advantageous:

(1) antigen-induced enhanced "leukocyte inhibitory factory" ("LIF")

(2) augmented production of interleukin-2 ("IL-2"), stimulated by mitogen, antigen, or alloantigen;

(3) enhanced generation of cytotoxic cells to Raji cells (a tumor line which grows in culture);

(4) augmented production of gamma-interferon, stimulated by mitogen or antigen; and (5) enhanced expression of high-density receptors for IL-2.

The inventor has found that Beta-1.0 and Zeta-2 displayed at least three out of the five new assay criteria as well as the enhanced DH response. However, since these materials are endogenous rather than synthetic, they vary in biological activity from time to time and depending on donor population.

The LIF assay is described in Gottlieb et al., *Modulation of Human T Cell Production*, J. Immunology 132: 256-260 (Jan. 1984), at p. 257. Protocols for the other assays are believed to be known to those skilled in this art. A convenient reference for the gamma-interferon assay in Sinha et al., Bio/Technology 6:810 (1988), at pp. 814-15.

As stated above, it has been shown that materials of the preceding examples have amplifier activity. The following examples illustrate this.

EXAMPLE 6

DH Assay of Beta-1.0

Serial dilutions of Beta-1.0 or preceding Example 2 were made from a solution containing the amplifier material derived from $4 \times 10^8$ buffy coat leukocytes in 1 ml of aqueous saline solution.

Tetanus toxoid was selected as the antigen to challenge the immune system of the patient. To 0.05 ml of tetanus toxoid, fluid diluted to 1/10 to 1/40 so as to elicit a small (preferably slightly less than $5 \times 5$ mm) skin reaction from the patient, 0.1 ml of the diluted Beta-1.0 preparation was added. The patient was subcutaneously injected with several different dilutions of Beta-1.0, and also with an equal quantity of tetanus toxoid (TT) without any Beta-1.0 added thereto. Two approximately perpendicular diameters of each responding skin site on the man's arm were measured at the times indicated below. ("TT+_" refers to TT and a dilution of Beta to the concentration indicated; "TT" alone is TT without Beta-1.0.)

At 5 hours, the respective responses to $TT + 10^{-8}$, $TT + 10^{-9}$, and TT were $14 \times 14$ mm, $19 \times 14$, and $3 \times 3$. At 24 hours: $20 \times 24$ mm, $19 \times 23$, $14 \times 12$. Other dilutions of Beta-1.0 produced less response.

EXAMPLE 7

DH Assay of Beta-1.11

Example 6 was repeated with serial dilutions of Beta-1.11 (endogenous YG-material), beginning with 1 microgram per microliter (ug/ul) of the product of Example 5. It is estimated that 100 pg of the product of Example 5 is the amount of Beta-1.11 that can be derived from approximately $3 \times 10^8$ buffy coat leukocytes. It is also estimated that the M.W. of Beta-1.11 is approximately 239. Hence, 1 ug/ul is approximately a 4 mM solution. Dilutions of 4 fM and 0.4 fM were prepared.

After following the procedure described in Example 6, it was observed that at 5 hours, the respective responses to TT+0.1 ml 4 fM, TT+0.1 ml 0.4 fM, and TT were $7 \times 8$ mm, $9 \times 9$, and $3 \times 5$. At 24 hours: $18 \times 21$ mm, $19 \times 19$, $14 \times 15$. Other dilutions of Beta-1.11 produced less response.

EXAMPLE 7A

Second Beta-1.11 DH Assay

Example 7 was repeated with serial dilutions of Beta-1.11 (endogenous YG-material), beginning with 53 nM solution of the product of Example 5. Serial dilutions of $10^{-6}$, $10^{-7}$, $10^{-8}$, and $10^{-9}$ were prepared; a saline control was also used. TT was diluted 1/20. Erythema was measured (mm $\times$ mm) and induration was scored on a scale of 0 to +++. The following data were observed (and are published in Sinha et al., Bio/Tech. 6:810–15 (1988), at p. 812):

|  | Hours Post Injection | | | |
| --- | --- | --- | --- | --- |
|  | 7 Hrs | | 12 Hrs | |
| Dilution | Erythema | Indur. | Erythema | Indur. |
| $10^{-6}$ | $14 \times 10$ | 0 | $18 \times 18$ | 0 |
| $10^{-7}$ | $12 \times 15$ | + | $15 \times 25$ | 0 |
| $10^{-8}$ | $12 \times 17$ | ++ | $20 \times 22$ | 0 |
| $10^{-9}$ | $10 \times 12$ | + | $20 \times 21$ | ± |

-continued

|  | Hours Post Injection | | | |
| --- | --- | --- | --- | --- |
|  | 7 Hrs | | 12 Hrs | |
| Dilution | Erythema | Indur. | Erythema | Indur. |
| Saline Ctl. | $4 \times 5$ | 0 | $10 \times 10$ | 0 | sharp, narrow peak of UV absorption at 210 nk sharp, narrow peak of UV absorption at 210 nk

EXAMPLE 8

DH Assay of Beta-1.12

Example 6 was repeated with serial dilutions of Beta-1.12 (endogenous YGG-material), beginning with 1 ug/ul of the product of Example 5. It is estimated that 3 ng of the product of Example 5 is the amount of Beta-1.12 that can be derived from approximately $1 \times 10^{12}$ buffy coat leukocytes. It is also estimated that the M.W. of Beta-1.12 is approximately 295. Hence, 1 ug/ul is approximately a 3 mM solution. Dilutions to 3 fM and 0.3 fM were prepared.

After following the procedure described in Example 6, it was observed that at 5 ours, the respective responses to TT+0.1 ml 3 fM, TT+0.1 ml 0.3 fM, and TT were $7 \times 8$ mm, $9 \times 9$, and $3 \times 5$. At 24 hours: $18 \times 21$ mm, $19 \times 19$, $14 \times 15$. Other dilutions of Beta-1.12 produced less response.

EXAMPLE 8A

Second Beta-1.12 DH Assay

Example 8 was repeated with serial dilutions of Beta-1.12 (endogenous YGG-material), beginning with 64 nM solution of the product of Example 5. Serial dilutions of $10^{-6}$, $10^{-7}$, $10^{-8}$, and $10^{-9}$ were prepared; two saline controls were also used. TT was diluted 1/80. Erythema was measured (mm $\times$ mm) and induration was scored on a scale of 0 to +++. The following data were observed (and are published in Sinha et al., Bio/Tech. 6:810–15 (1988), at p. 812):

|  | Hours Post Injection | | | |
| --- | --- | --- | --- | --- |
|  | 7 Hrs | | 12 Hrs | |
| Dilution | Erythema | Indur. | Erythema | Indur. |
| $10^{-6}$ | $2 \times 2$ | 0 | 0 | 0 |
| $10^{-7}$ | $9 \times 10$ | + | $16 \times 16$ | + |
| $10^{-8}$ | $12 \times 13$ | ++ | $18 \times 21$ | ++ |
| $10^{-9}$ | $10 \times 13$ | ++ | $16 \times 17$ | + |
| L Saline Ctl. | $8 \times 10$ | + | $16 \times 17$ | + |
| R Saline Ctl. | $8 \times 8$ | + | $16 \times 17$ | + |

EXAMPLE 8B

DH Assay of Beta-1.13

Example 6 was repeated with serial dilutions of Beta-1.13 (third endogenous material), beginning with 1 ug/ul of the product of Example 5. It is estimated that 3 ng of the product of Example 5 is the amount of Beta-1.13 that can be derived from approximately $1 \times 10^{10}$ buffy coat leukocytes. It is also estimated that the M.W. of Beta-1.13 is approximately 400. Hence, 1 ug/ul is approximately a 2.5 mM solution. Dilutions to 2.5 fM and 0.25 fM were prepared.

After following the procedure described in Example 6, it was observed that at 5 hours, the respective responses to TT+0.1 ml 2.5 fM, TT+0.1 ml 0.25 fM, and TT were $11 \times 17$ mm, $10 \times 16$, and $9 \times 9$. At 24 hours:

13×12 mm, 14×12, 6×9. Other dilutions of Beta-1.13 produced less response.

EXAMPLE 9

Effect of Beta-1.11 and T-helper Cell IL-2 Receptor Expression

Serial dilutions of Beta-1.11 were prepared, beginning with a 81.3 nM concentration and then serially diluting that further by factors of 1000, 2000, 4000 ... 512,000. the 1/512,000 dilution produces a preparation that is a 159 fM concentration of Beta-1.11.

A tetanus toxoid (TT) preparation was prepared of strength 0.1 flocculation unit ($L_f$) per ml.

Cell cultures were prepared with the TT preparation alone, and with the TT preparation combined with the serial dilutions of Beta-1.11. The cultures were incubated and mixed with a suitable antibody against IL-2 receptors. Data for receptor expression was tabulated both for T-helper cells bearing a low density of receptors and for T-helper cells bearing a high density of receptors. (The T-helper cells bearing a high density of receptors are considered to be the ones that are immunologically active.) The cells were from normal subjects.

In the case of the TT preparation alone, 4.7% of T-helper cells expressed a low density of IL-2 receptors and 0.4% of T-helper cells expressed a high density of IL-2 receptors.

There was a plateau of maximal expression for T-helper cells bearing a low density of receptors from TT+20.3 pM Beta-1.11 (9.9% expression) to TT+1.3 pM (8.4%). The highest figure for high density of receptors was at 159 fM (9.9%). This highest figure occurred at a point where there was a steadily ascending curve. Accordingly, it is believed that if further dilutions of Beta-1.11 had been used a still higher figure would have been reached, before the expression percentage began to drop. It is not possible to state, from this data, where the maximum would occur, bit it seems likely to be somewhere between 80 fM and 20 fM.

The low density plateau reflected an approximately doubled expression rate of IL-2 receptors as a result of Beta-1.11. The high density maximum, which the inventor considers more relevant, reflected an increase of IL-2 receptors by a factor of approximately 25 as a result of Beta-1.11, and that figure probably falls short of the increase that would result from using still more diluted Beta-1.11.

EXAMPLE 10

Effect of Beta-1.11 on Antigen-Induced Production of Gamma Interferon

Preparations of 0.1 $L_f$/ml and 1.0 $L_f$/ml TT were used to determine the effect of Beta-1.11 (endogenous YG-material) on production of gamma-interferon in normal cells. As before, serial dilutions of Beta-1.11 were prepared from 46.5 pM to 91 fM.

The 0.1 $L_f$/ml and 1.0 $L_f$/ml TT preparations, alone, respectively induced baseline production of 1.0 and 10.4 units/ml of gamma-interferon.

0.1 $L_f$/ml TT+317 fM Beta-1.11 produced 29.8 units/ml, the observed maximum, and 0.1 $L_f$/ml TT+91 fM Beta-1.11 produced 29.1 units/ml.

1.0 $L_f$/ml TT+159 fM produced 25.6 units/ml, the maximum.

In the case of the 0.1 $L_f$/ml TT preparation, the maximum was approximately 30 times the baseline amount.

In the case of the 1.0 $L_f$/ml TT preparation, the maximum was approximately 2.5 times the baseline amount.

Generally, the DH assays shows that of Beta-1.11, Beta-1.12, and Beta-1.13 are immunologically active and they appear to be more active (per unit weight) than Beta-1.0, in the setting of these assays. The apparent increase in potency may be attributed to the elimination of phenylalanine and other amino acid products, which are without intrinsic immunological activity.

In both of the TT+Beta-1.11 in vitro immunological tests, expression of high-density IL-2 receptors and antigen-induced production of gamma-interferon, the optimal concentration of Beta-1.11 appears to be approximately 300 fM. Since workers in this field consider these two assays generally indicative of immunological effect, and since they have been found correlated to clinical immunological effect in the case of other Beta materials from which Beta-1.11 is derived, the inventor considered that the assays indicated a very high probability that Beta-1.11 would produce in vivo amplifier effect in human subjects. As shown below (Examples 17–18), this prediction has been confirmed by actual clinical data. Thus, the materials of this invention have been shown to stimulate gamma interferon production and to enhance expression of receptors for IL-2. These are among the most important known effects of biological responses produced in lymphocytes.

In the case of Beta-1.12, it is not certain whether the DH response is to the Beta-1.12 per se (i.e., to material essentially consisting of endogenous YGG-material) or to a Beta-1.11 metabolite (i.e, material consisting essentially of endogenous YG-material) of Beta-1.12. It is known that pentapeptides (enkephalins) containing a YGG amino acid residue sequence are degraded in vivo by the action of dipeptidylaminopeptidase, which hydrolyzes enkephalins (e.g., $H_2N$-Tyr-Gly-Gly-Phe-Met-OH) by cleaving the Gly-Gly amine bond. (See, e.g., Schwartz et al., op. cit. supra (Background section of specification), at p. 1716, citing and summarizing studies in this field.) Hence the apparent immunoamplificatory effect of YGG-material might be attributable to YG-material as a metabolite of YGG-material rather than to YGG-material itself.

On the other hand, both endogenous peptide materials may have intrinsic immunoamplificatory effect. For example, the receptor site for this lymphokine could be associated with the Tyr-Gly portion of the molecule, and the additional Gly amino acid residue may have a neutral effect on reception and biological activity. It is also possible that YGG interacts with a different receptor site to have the same biological effect as YG. Alternatively, a complex of both peptides, perhaps through a trace metal (such as $Zn^{++}$, $Ca^{++}$, $Fe^{++}$, $Mn^{++}$, or $Mg^{++}$) may be required. This is a question calling for further work, such as in vitro tests of Tyr-Gly-Gly in the presence of a suitable aminopeptides inhibitor, to prevent cleavage of the Gly-Gly amide bond in Tyr-Gly-Gly to produce Tyr-Gly. At the present, the inventor believes it proper to conclude only that the YGG data show a potent direct or indirect immunoamplificatory effect.

In the case of Beta-1.13, the entire immunological activity is attributable to Beta-1.13 itself, since there is no reason to consider its ring, non-peptide molecule to be a metabolite of either of the peptide molecules.

EXAMPLE 11

DH Assay of Zeta-2

The procedure of Example 6 was repeated with Zeta-2 of Example 5. However, purified protein derivative of tuberculin ("PPD") was substituted for TT.

At 12 hours, the respective responses to $PPD+10^{-6}$, $PPD+10^{-7}$, $PPD+10^{-8}$, and PPD were $1\times1$ mm, $15\times22$, $14\times11$, and $1\times1$. At 27 hours: $2\times2$ mm, $24\times24$, $15\times15$, and $3\times3$.

III. Human Therapy Tests of Endogenous Amplifier Materials

The effectiveness of above-described endogenous amplifier materials in amplifying human immune system response has been tested in a number of men suffering from AIDS or ARC. All amplifier materials used in this work were free of endotoxin as detected by the Limulus assay (M.A. Bioproducts, Rockville, Md.). All material used was also pyrogen-free. The following examples illustrate these tests. (As used hereinafter, the term "T-helper cell" includes cells designed as T4+, CD4+, Leu3+, and T4.)

The inventor has ascertained by empirical means that an effective dosage amount of these products, in the procedures described hereinafter, is that derived from 125,000 leukocytes, purified by the method of Example 2 and dispensed in 0.5 ml of normal sterile saline solution. (This dosage amount, that derived from 125,000 leukocytes, is frequently referred to hereinafter as "one standard dose of Beta.")

EXAMPLE 12

Multiple Doses of Beta-1.0 With Transfusion

An AIDS patient, DT, with Kaposi's sarcoma was given doses of Beta-1.0 (a preparation containing YG-material, YGG-material, phenylalanine, and other materials) together with transfusions of isologous leukocytes available from DT's identical twin brother (a normal, disease-free person). DT also received such transfusions without Beta-1.0.

An initial transfusion of approximately $1.0\times10^{10}$ isologous leukocytes (without Beta-1.0) produced a moderate restoration of DT's phytohemagglutin (PHA) proliferative response. Within 13 days the response declined to baseline levels with no concomitant alteration in the ratio of circulating helper leukocytes to suppressor leukocytes (T4/T8 ratio).

Ten days after the initial transfusion, DT was given a single standard dose of Beta-1.0 (as stated above, that which is derived from 400,000 leukocytes). No effect was observed on DT's PHA response.

A cycle of treatment comprised of a second isologous leukocyte transfusion (again, the same number of leukocytes) followed at 24, 48, and 71 hours by subcutaneous administration of Beta-1.0 doses derived from 400,000, 4,000,000, and 400,000 leukocytes, respectively. A significant increase in DT's PHA responsiveness followed. It was associated with an increase in the T4/T8 ratio, resulting from an absolute increase of T4+ cells and a decrease in T8+ cell numbers. After approximately one month, these parameters of immune system response declined to approximately their former level.

A third transfusion similar to the first (no Beta-1.0) was given. No effect on PHA response or T4/T8 ratio was observed.

While these studies were made, parallel studies of IL-2 production were made. Initially, no IL-2 production was observed in response to PHA. This correlated with the patient's low proliferative response to mitogen. The initial leukocyte transfusion did not affect this parameter. After the second transfusion (leukocytes and Beta-1.0), significant levels of IL-2 were induced by PHA. It is considered that this data (and similar data in the next two examples) confirms the in vitro data of Examples 9–10 and the discussion following those examples, concerning stimulation of lymopholine production.

EXAMPLE 13

Multiple Doses of Beta-1.0: Group 1

The members of a group of 15 patients with AIDs or ARC received one standard dose of Beta-1.0 once every month until three doses were given (three months). Of these 15 patients, six had candida infections (oran candidisis), and 12 has Kaposi's Sarcoma.

Clinical symptoms were monitored. No decrease in weight was observed. No toxicity to Beta-1.0 was observed.

A significant decrease in candida infection was observed as a result of treatment, in three-quarters of the patients completing the monthly dose protocol.

Skin test sensitivity (DH test) to tetanus toxoid was noticeably enhanced, and may be considered to have returned to an approximately normally level in 47% of the subjects. Since, according to the Walter Reed Classification of Severity of AIDS/ARC (see 314 New Eng. J. Med. 131 (1986)), candida infection and loss of skin test sensitivity are signs of far advanced immunodeficiency, it is considered that the effectiveness of Beta-1.0 in reversing these symptoms is medically significant.

Mitogen-stimulated leukocyte proliferation increased with each successive dose. Mitogen-stimulated IL-2 production increased in at least 60% of patients. Response to pokeweed mitogen (PWM) increased for those patients having more than 50–100 T4 cells per $mm^3$ remaining.

EXAMPLE 14

Multiple Doses of Beta-1.0: Group 2

The members of a group of 14 patients with AIDS or ARC received one standard dose of Beta-1.0 every two weeks for six doses (approximately three months). Of these subjects, six had candida infected dose of Beta-1.0 every two weeks for six doses (approximately three months). Of these subjects, six had candida infections. Of the 14 patients, 11 had Kaposi's Sarcoma.

Clinical symptoms were monitored. Eleven of the 14 patients gained weight. An average weight gain of 4.4 lb occurred in these 11. No toxicity to Beta-1.0 was observed. Serum uric acid levels fell. Creatine phosphokinase levels fell. Since high levels of uric acid and creatine phosphokinase reflect tissue breakdown characteristic of AIDS, it is considered that lowering of the levels of these substances and reversal of weight loss suggests significant clinical improvement.

Skin test sensitivity to tetanus toxoid returned in 57% of subjects. Candida infection was totally cleared in three subjects and decreased in another.

Mitogen-stimulated leukocyte proliferation increased. Mitogen-stimulated IL-2 production increased in 60% of patients after two doses of Beta-1.0; and in all those patients having more than 50–100 T-helper cells/$mm^3$ remaining, after two doses of Beta-1.0.

Response to pokeweed mitogen (PWM) increased for those patients having more than 50-100 T-helper cells/mm$^3$ remaining. A small increase to PWM appeared after the scanned dose with those patients having fewer than 50-100 T-helper cells/mm$^3$ remaining, and slowly increased following the next two doses.

There was also observed a slowing of the rate of destruction of T-helper cells in these AIDS and ARC patients during their treatment with Beta-1.0. For example, untreated patients with ARC typically loss T-helper cells at the rate of approximately 13.4 cells/month. For those ARC patients who received Beta-1.0 on a monthly basis (Example 13), the rate of T-helper cell loss was 7.2 cells/month, while for those who received it every two weeks (Example 14) the rate of T-helper cell loss was 4.2 cells/month. It is believed that this data indicates that Beta-1.0 slows the rate of T-helper cell destruction typical of ARC, and that the retarding of destruction was proportional here to the dosage.

EXAMPLE 15

Multiple Doses of Beta-1.0: Group 3

Five patients, three with AIDS (RB, JB, and RG) and two with ARC (WW and CM) were treated with Beta-1.0 over a period of approximately a year or more. (One standard dose administered intradermally every two weeks.)

Skin test sensitivity returned completely in three subjects and partially in one (RB, JB, WW, and CM). Candida infection improved in the two patients (RB and CM) initially having it and it did not appear in the others. The percentage of T-helper cells increased transiently in four patients (RB, RG, WW, and CM).

Three patients gained substantial weight (RB, WW, and CM). PHA-stimulated lymphocyte proliferation increased in all five, PWM response in four (RB, RG, WW and CM), IL-2 production in three (RB, WW, and CM).

A sixth patient was originally included in this group, but his immunodeficiency was so severe on presentation that he succumbed to an overwhelming opportunistic infection before immunological reconstitution could be effected.

EXAMPLE 16

AIDS/ARC Conversion in Multicenter Tests of Beta-1.0

In order to secure clinical data for FDA licensing of Beta-1.0, double-blind, randomized, placebo-controlled trials were conducted on a total of 141 ARC patients at eight testing centers, over a six-month period.

93 patients diagnosed as having ARC received one standard dose of Beta-1.0 biweekly for 26 weeks. 48 patients diagnosed as having ARC received a placebo dose biweekly for 26 weeks. Attending physicians monitored the patients for clinical symptoms.

In particular, focus was directed to diagnosis of the conversion to AIDS in these ARC patients. This conversion is marked by a significant change in symptoms and clinical status, such as development of Pneumocytis carinii pneumonia, tracheobronchial candidiasis, or Kaposi's Sarcoma. Such a clinical event is termed an "endpoint," since it marks the end of ARC and the beginning of AIDS, which appears to be invariable fatal, and is attached by more severe clinical symptoms.

At the end of 26 weeks, endpoints had appeared in 12 of the 48 placebo patients, representing 25% of that population; and in 4 of the 93 patients given Beta-1.0, representing 4% of that population. The rate of ARC/AIDS conversion in patients treated with Beta-1.0 was thus approximately 20% of the conversion rate in placebo patients. Since ARC/AIDS conversion is clinically highly significant, it is believed that the foregoing trial data supports FDA licensure of Beta-1.0 for ARC patients, to delay conversion to AIDS; and the data has been submitted to FDA for that purpose.

The patients treated with Beta-1.0 in these trials were also observed to show improved clinical symptomatology comparable to that described above in Examples 13–14, such as lessened weight loss, and less coughing and diarrhea.

EXAMPLE 17

Three-month Dosage of Beta-1.11 (ARC Patient)

ARC patient A received a total of six doses of 0.1 pg of Beta-1.11 (endogenous YG-material), given biweekly for approximately three months. His immune responsiveness was measured by determining the reactivity of his leukocytes to pokeweed mitogen (PWM).

A baseline responsiveness was established before treatment at 6241 units, hereinafter designated as 100%, for comparison purposes. His subsequent PWM reactivity measurements are tabulated below:

| Response after Dose No. | Units | Percent |
|---|---|---|
| 0 (baseline) | 6,241 | 100% |
| 1 | 14,027 | 225 |
| 2 | 13,875 | 222 |
| 3 | 12,058 | 193 |
| 4 | 11,753 | 188 |
| 5 | 10,358 | 166 |

It was also observed that A regained his DH reaction to tetanus toxoid as a result of treatment with Beta-1.11. The foregoing data indicated that dosage was endogenous YG-material at least partially reversed this patient's immunodeficiency.

The trend of observed PWM reactivity suggests that the effect of 0.1 pg was less after several doses had been administered, and that lower doses should be used for subsequent treatment. That is, a dose that is optimal on starting therapy will in some instances have to be reduced as time goes on. The inventor has observed that there is no optimal dosage of amplifier, and that doses above or below the optimum amount produce less amplifier effect than the optimal dose does (see, e.g., Gottlieb U.S. Pat. No. 4,468,379, col. 13–14, 16–17; copending application, Diagnostic methods for immune function, Ser. No. 830,728, now issued as U.S. Pat. No. 4,778,750, Sections III–IV, cols. 5–7).

EXAMPLE 18

Two-month Dosage of Beta-1.11 (ARC Patient)

ARC patient B had previously been treated with a series of standard doses of Beta-1.0 (a preparation containing endogenous YG-material, endogenous YGG-material, phenylalanine, and other material) to reconstitute his immune system. He was then given biweekly doses of 0.1 pg of Beta-1.11 (endogenous YG-material) for a total of four doses.

His immune function was measured by determining PWM reactivity, as in the case of Patient A. His reactivity throughout remained at slightly below normal levels. His DH response to tetanus toxoid also remained at slightly below normal levels. The foregoing data indicate that dosage with endogenous YG-material maintains in effect the restoration of immunodeficiency brought about by dosage with Beta-1.0.

The data for Patient B suggest that 0.1 pg was approximately the correct dosage amount for this patient (i.e., an effective dosage amount).

The foregoing examples suggest that endogenous YG-material (Beta-1.11) and materials containing it (such as Beta-1.0) stimulate the T-helper cell population of the human body. This suggests that Beta materials are useful in improving human immune response characterized by a T-helper cell defect, by amplifying immune responsiveness. It is believed that doses of Beta partially restore the functioning of a defective subset of the T-helper lymphocytes. Tests such as that conducted on patient DT suggest that Beta can partially correct a defect in T-helper cell function even in the presence of the excessive proportions of T8+ cells observed in AIDS patients. It appears, further, that some minimal level of residual T-helper cell function must be present for Beta to amplify and thus improve immunological functions; if T-helper cell loss is too severe, there may not be enough T-helper cells left to respond to doses of Beta as a lymphokine and thus be immunologically reconstituted. The data above suggest that when the total T-helper cell population falls below approximately 100 cells/mm$^3$, it is difficult or impossible to reconstitute immunological function.

Generally speaking, 0.5 to 5.0 pg of Beta-1.11 (endogenous YG-material) or 0.5 to 5 ng of Beta-1.0 (including approximately 90% phenylalanine), administered biweekly by intradermal or subcutaneous injection, are effective dosage amounts for adult male (70 kg) AIDS or ARC patients. Those dosages are approximately equivalent to 7 to 70 fg of YG/kg and 7 to 75 pg of Beta-1.0/kg, respectively. Because of patient-to-patient individual variations, the difference in various immunodeficient clinical conditions, and the need to allow exercise of professional judgment by the attending physician, these dosage amounts must be considered subject to change by a factor of 5 to 10 in each direction. It should be noted that, since the GMW of YG is approximately 239, 7–70 fg/kg represents approximately 0.03–0.3 f moles of YG/kg. The 7–70 fg of YG/kg dosage amount, varied by the stated factor of 10 each way, translates to approximately 0.5 to 500 fg/kg or, in molar terms, from $3\times10^{-18}$ moles/kg to 3 fM/kg. As previously indicated, endogenous YG-material is accompanied in the natural state by endogenous YGG-material, in an amount averaging approximately 5% YGG:YG; however, the YGG:YG ratio varies from samples to sample and may range from approximately 1/50 to 1/5. Thus, the aforesaid 0.5 to 500 fg/kg of YG-material is accompanied by from 0.01 to 100 fg/kg of YGG-material in natural samples. By the same token, the aforesaid molar values of from $3\times10^{-18}$ moles/kg to 3 fM/kg of YG-material are accompanied by from approximately $5\times10^{-21}$ moles/kg to 0.5 fM/kg of YGG-material.

The above-described clinical work has primarily been that conducted with IMREG-1, which has been found to be a mixture of Beta-1.11 (endogenous YG-material), Beta-1.12 (endogenous YGG-material), phenylalanine, Phe-Ser, Gly-Gly, Gly-Glu, and amounts of some other amino acid products. It is believed desirable to administer a standardized product to patients, rather than a variable biological product whose constituents differ from dose to dose depending on the source material. Thus, it is considered that it would probably be preferably to administer a predetermined mixture of Beta-1.11 (endogenous YG-material), Beta-1.12 (endogenous YGG-material), and perhaps other material, rather than unstandardized IMREG-1, subject of course to regulatory constraints.

This suggests a preferred procedure for using endogenous materials in which purification to the Beta-1.11, Beta-1.12, and Beta-1.13 level is carried out. That is followed by remixture in accordance with a predetermined formula. As indicated elsewhere, the average ratio of YG:YGG:Beta-1.13 in IMREG-1 has been found to be approximately 18:1:1. If, as may be the case, the three amplifiers must be concurrently present for optimal biological results, the predetermined mixture should contain them in approximately that ratio (approximately 90%/5%/5%). The inventor considers that this ratio should be subject to a range of from approximately 10:1:1 to 25:1:1, paralleling natural variations in the proportion of materials in different human samples.

It is as yet not ascertained whether the phenylalanine, Phe-Ser, Gly-Gly, Gly-Glu, and amounts of some other amino acid products present in IMREG-1 contribute anything to immunological activity. It has been shown that these components lack detectable intrinsic immunological activity. However, that does not rule out the possibility that they may act as stabilizers, preventers of hydrolysis, or otherwise as adjuncts of the intrinsically active components. Therefore, clinical work may show that the predetermined mixture discussed in the preceding several paragraphs should contain some of these components, which were actually present in the product (IMREG-1) primarily used in clinical tests with AIDS and ARC patients. Hence, the predetermined mixture may appropriately include phenylalanine, Phe-Ser, Gly-Gly, and Gly-Glu. This would provide a standardized product and yet one more closely parallelling the combination of the IMREG-1 material used in large scale clinical tests with AIDS and ARC patients.

It is contemplated that the above described mixture would be packaged in a vial, in a sterile saline solution, or in a prefilled syringe, again in sterile saline. All of the inventor's large-scale clinical work to date has utilized vials of IMREG-1 in sterile saline solution. However, it would be inappropriate to rule out suppositories, or tablets, capsules, and other oral dosage formats, given a suitable delivery mechanism.

The following present-tense example is intended to illustrate and summarize the teachings of the preceding examples describing actual clinical data with AIDS and ARC patients.

EXAMPLE 19

Increase of Immune Response

A patient is known to suffer from immunodeficiency. The immunodeficiency may be attributed to AIDS, ARC, chemotherapy, radiation treatment, or another known cause of immunodeficiency.

Endogenous amplifiers are prepared and purified as described in Section I, supra, and are pooled, lyophilized, and redissolved in normal saline or other physiologically acceptable vehicles. An effective dose (e.g., 0.1 ml containing the amount of material extracted from $4\times10^5$ leukocytes) is injected intradermally. Increased immune responsiveness occurs and is monitored by the patient's reactivity to an antigen to which he is known to be sensitive (e.g., tetanus toxoid), comparing reactivity before and after administering the amplifiers.

Amplifiers are further administered either individually, or in combination, depending upon the desired effects. The persistence of the systemic modulation produced by administration of the amplifiers varies from patient to patient, and must therefore be monitored periodically with a suitable sensitivity test, e.g., by DH assay as described above.

Additional doses are administered as required to maintain a desired amplification of immunity, based upon the professional judgment of the attending physician. That is, the dosage should be increased over that specified above, if immune responsiveness is insufficient (but not to the level where increasing doses decrease immune response); and the dosage should be decreased from that specified above, if immune responsiveness is greater than that which the physician considers appropriate.

As indicated in Example 6, Zeta-2 has immunoamplifier effect similar to that of Beta-1.0, although apparently slower in terms of onset of effect. In addition to increasing DH response, Zeta-2 was found to increase gamma interferon production and to enhance expression of IL-2 receptors, in vitro. From the foregoing in vivo and in vitro data, which those persons familiar with this field generally regard as important predictors of clinical immune response, the inventor concluded that Zeta-2 possess immunoamplifier activity similar to that of the Beta group.

EXAMPLE 19A

Zeta-2 Immune Response

The procedures of Example 19 is repeated with another patient known to suffer from immunodeficiency. An effective dose (0.1 ml sterile saline containing the amount of material extracted from 125,000 leukocytes, tested for freedom from endotoxin and pyrogen) is injected intradermally, biweekly for 12 weeks.

The patient's reactivity to PPD (DH assay) increases. Mitogen-stimulated lymphocyte proliferation progressively increases with additional dosages. Mitogen-stimulated IL-2 production also increases.

The patient is retested six weeks after conclusion of the 12-week course. Reactivity to PPD, mitogen-stimulated lymphocyte proliferation, and mitogen-stimulated IL-2 production are found to be at approximately the initial (week-0) level.

It is concluded that administration of Zeta-2 increases immune responsiveness in the patient.

The foregoing discovery that human leukocyte dialysates contain endogenous amplifier materials, which can be extracted, purified, and administered to patients, is considered significant in several respects. First, it significant that these materials may be isolated from normal individuals, rather than from specific identified donors, because this permits (and in fact has actually led to) large-scale purification of the materials from pooled sources. Second, the discovery that some endogenous amplifier material contains as intrinsically active components low-M.W. peptide products opens the way to basically chemical, rather than basically biological, preparation of amplifier compositions. This matter is discussed in the following section of the specification. Furthermore, as described in more detail below, this discovery also paves the way to molecular manipulation of the products already discovered, in order to improve their pharmaceutical properties.

IV. In Vitro and in Vivo Tests of Synthetic Amplifiers

A. Synthetic YG

The endogenous product designated above as Beta-1.11 has been shown, by amino acid analysis, to consist essentially of YG-material. It is not now known, and may not be ascertainable in the present state of the art, whether the YG of endogenous YG-material exists as a simple YG molecule or as a more complex molecule, such as an ester, salt, and so on.

As indicated in the Background section, YG exists as a commercial synthetic product. The inventor has discovered a process for purifying it to U.S.P. grade or equivalent, and has discovered that the product possesses intrinsic amplifier activity. In the following section of this specification, in vitro and in vivo assay data is described for synthetic YG. All references to commercial grade YG are to commercially available L-tyrosylglycylglycine (Sigma Chem. Co., St. Louis, Mo.). Commercial YG is not sold in U.S.P. grade, and it is not lawful to sell the product as a drug (pharmaceutical), as "drug" is defined by federal law. Commercial grade YG contains pyrogens and endotoxin, among other medically unacceptable components. The following procedure makes available for the first time a L-tyrosylglycylglycine product free of pyrogens, endotoxin, and other medically unacceptable contaminants.

EXAMPLE 20

Purification of YG

Commercial grade YG was purified of pharmaceutically unacceptable constituents or contaminants by the following procedure: 1 ug of YG was dissolved in 1 ul of normal saline, and was then added to 99 ul of 0.05% trifluoroacetic acid aqueous solution.

50 ul of the resulting solution was injected into a reverse-phase high-pressure liquid chromatography analytic column (ODS Analytic Column, DuPont Zorbax TM, 4.6 mm×25 cm). The column was eluted with the following combination of linear gradients, using HPLC grade 100% acetonitrile against 0.05% trifluoroacetic acid aqueous solution as solvent, 1 ml/min flow rate: (1) from 0 min to 15 min. 0% to 6% acetonitrile concentration; (2) from 15 min to 45 min, 6% to 40% acetonitrile concentration.

Absorbance was monitored at 210 nm, 0.05 O.D. units full scale. A sharp, narrow peak occurred at approximately 16.0 to 17.0 min, much higher than any other peaks. The elutant accompanying the peak was purified YG, substantially free of contaminants. Specifically, the material was found to be free of endotoxin and pyrogen.

EXAMPLE 21

DH Assay of YG/YGG

Purified synthetic YG of Example 20 and purified synthetic YGG of Example 1 of Gottlieb U.S. Pat. No. 4,699,898 were dissolved into sterile saline, in a 2:1 ratio, to concentrations, respectively, of 220 nM and 110 nM. (This mixture had an effective amplifier concentration of 330 nM.) Further 1:10 successive dilutions of this mixture into sterile saline were prepared, to provide mixtures containing 220 fM, 22 fM, 2.2 fM, and 0.22 fM concentrations of YG.

Samples of 0.1 ml of each dilution were injected intradermally into a normal human volunteer, a 70 kg adult male, in combination with a known recall antigen—tetanus toxoid (TT), 0.05 ml, 1/40 dilution of standard (Squibb/Connaught). As a control, the same amount of TT was injected with 0.1 ml normal sterile saline (0 fM YG).

The following lesions were observed (mm×mm) at the times indicated:

| YGConc. | 220 fM | 22 fM | 2.2 fM | 0.22 fM | 0 fM |
| --- | --- | --- | --- | --- | --- |
| 6 hr. | 7 × 6 | 7 × 8 | 7 × 5 | 4 × 4 | 7 × 4 |
| 12 hr. | 6 × 5 | 13 × 13 | 10 × 6 | 8 × 5 | 6 × 5 |
| 24 hr. | 3 × 4 | 10 × 9 | 10 × 9 | 7 × 7 | 3 × 2 |

EXAMPLE 21A

Another DH Assay of YG/YGG

The procedure of Example 21 was repeated five weeks later, using the same normal test subject and the same reagents. The purpose was to show normal human variability in DH response as modulated by these amplifiers, in a single subject over time.

The following lesions were observed (mm×mm) at the times indicated:

| YGConc. | 220 fM | 22 fM | 2.2 fM | 0.22 fM | 0 fM |
| --- | --- | --- | --- | --- | --- |
| 6 hr. | 6 × 5 | 7 × 8 | 6 × 5 | 3 × 4 | 5 × 5 |
| 12 hr. | 12 × 13 | 16 × 16 | 17 × 14 | 15 × 12 | 12 × 12 |
| 24 hr. | 4 × 4 | 3 × 3 | 6 × 6 | 4 × 4 | 6 × 9 |

EXAMPLE 22

Tyr+Gly DH Assay

As another control, the procedure of Example 21 was carried out with a mixture of the single amino acids Tyr and Gly, in place of the mixture of YG and YGG used in Examples 21 and 21A. The same amount of TT was used. This test was carried out two weeks before Example 21, on the same subject.

The following lesions were observed (mm×mm) at the times indicated:

| T + G Conc. | 220 fM | 22 fM | 2.2 fM | 0.22 fM | 0 fM |
| --- | --- | --- | --- | --- | --- |
| 6 hr. | 0 × 0 | 0 × 0 | 0 × 0 | 0 × 0 | 0 × 0 |
| 12 hr. | 6 × 5 | 5 × 4 | 4 × 4 | 3 × 3 | 3 × 3 |
| 24 hr. | 11 × 10 | 12 × 13 | 12 × 13 | 10 × 9 | 10 × 11 |

In addition, reference should be made to the Sinha et al. paper in 6 Bio/Technology 814 (1988). In Table 3 of the paper, the data comparing the immunological activity of synthetic YG (referred to as B4) with that of endogenous YG-material (referred to a ZB-4) indicated that endogenous YG-material was 10 to 20 times as active as synthetic YG in inducing formation in vitro of gamma interferon. This data supersedes some earlier and more limited data of the inventor in which it appeared that synthetic YG was slightly more potent (about half an order of magnitude) then endogenous YG-material in inducing formation in vitro of gamma interferon.

It is noted that in Examples 21 and 21A, using a synthetic YG/YGG material, amplification of DH response was seen in the range of 2.2 fM to 22 fM YG (or 3.3 fM to 33 fM total amplifier). This may be compared with the assays of Examples 6–8, in which DH tests were performed with Beta-1.0 (mixture of endogenous YG-material and YGG-material, with extraneous material present), Beta-1.11 (endogenous YG-material), and Beta-1.12 (endogenous YGG-material). These tests suggest a greater potency on the part of the endogenous products. No significant effect on DH response to TT was seen with the mixture of single amino acids.

Strictly speaking, the results of the DH assay of synthetic YG/YGG of Examples 21–21A cannot be compared precisely with the DH assays and endogenous YG-material and endogenous YGG-material of Examples 7–8, because different human test subjects were used in the tests of synthetic and endogenous materials. The results of these four assays, however, are consistent with the inventor's empirical observations that, speaking very, very approximately, the synthetic amplifier compounds YG and YGG are an order of magnitude less potent than the corresponding endogenous amplifier materials Beta-1.11 and Beta-1.12. At this time, there is not a proper scientific basis on which to explain the seeming difference, although it is clear that the materials cannot be identical given this disparity in activity. Some possible hypotheses are stated below, at the end of this section.

EXAMPLE 23

T-helper Cell Receptor Expression Assay of YG

The T-helper cell receptor expression assay of Example 9 was repeated with synthetic YG of Example 20.

The highest figure for high-density of receptors was at approximately 22 fM, and reflected an increase of IL-2 receptors by a factor of approximately 1.6 as a result of YG. (This may be compared with Example 9 in which endogenous YG-material was most active at approximately the same molar concentration, but increased receptors by a factor of approximately 25.)

EXAMPLE 24

Mouse Tests of YG

Ten $BDF_1$ strain mice are divided into two groups of 5. Each mouse is injected with 100 L1210 leukemia cells from ascitic fluid of DBA/2 host mice.

The mice in Group I (control) are thereafter given injections of 0.1 ml sterile saline every third day. The mice in Group II are thereafter given intradermal injections of 2 fg of synthetic YG of Example 20 in 0.1 ml of sterile saline, every third day. The mice weigh approximately 20 g each, so that 2 fg represents approximately 100 fg/kg of bodyweight.

All of the mice are dead after approximately three weeks. The mean survival rate of the Group II mice is approximately 2.4 days loner than that of the Group I mice.

Synthetic YG has an immunological activity similar to that of endogenous YG-material. However, the synthetic compound appears to be less potent than the endogenous material. If the human-derived product were identical to the synthetic commercial chemical, this difference in activity should not occur. Since the difference did occur, that fact suggests that there must be some difference between the synthetic and endogenous products.

The discrepancy may be due to any of several possible causes. The synthetic commercial product may in whole or part be different isomeric forms from the endogenous products. The endogenous materials may be complexed, as discussed above, for example, with trace metal ions, such as Zn++. The endogenous materials may be more stable than the chemical materials, in vivo, because of chemical differences, or because of the presence of other endogenous materials. While the synthetic commercial product is simply the dipeptide, per se, rather than derivatives thereof, the endogenous products may contain substitutions such as a methyl, acetyl, or amide for an H, or other molecular variations may occur, which are not capable of being detected by the analytic procedures utilized here. Other endogenous materials accompanying the intrinsically active material may include phenylalanine, Phe-Ser, Gly-Gly, and Gly-Glu. (These have been found present in IMREG-1.)

It should be noted, however, that while the synthetic products purified from commercially available chemicals appear to be less active biologically, they are considerably cheaper to prepare. It is probable that the difference in activity is not a decisive factor in itself from a therapeutic standpoint; and it is believed that the synthetic product is more uniform in activity, from preparation to preparation, thereby permitting more reproducible (repeatable) results. The synthetic product is also free of the stigma attached to blood-derived products, which are often (correctly or incorrectly) believed to harbor viruses and other pathogens. The latter factors may well be more important, on balance, from a medical standpoint, than relatively lower activity, but that remains to be seen.

Consequently, there may be a tradeoff of factors leading to a conclusion that the chemically-derived synthetic products are biologically adequate, and are therefore the basis of a preferred commercial embodiment. But at this time it is not possible to ascertain definitely which embodiment is preferable.

B. Preparation and Assays of Synthetic Materials Chemically Related to YG and Other YGG-material It is believed that further synthetic versions of the endogenous YG-material described herein will be developed on the basis of further analytic work built on the information disclosed herein. It is further believed that such synthetic materials, when purified form unacceptable contaminants, may be considered preferable to the natural materials derived from human leukocyte extracts. For example, it is known that absorption rate and blood level of pharmaceuticals can be improved by molecular modifications of a natural or earlier-discovered form of a product. The historical literature contains numerous instances. Thus, chlortetracycline was dechlorinated to provide an improved tetracycline product; a double bond in clorothiazide was saturated to produce hydrochlorothiazide, thereby lowering the effective dosage amount by a factor of ten; and numerous synthetic forms of penicillin were provided by modifying the side chain attached to the beta lactam ring, such as by placing a benzyl at its end or replacing an H attached to the side chain with a $CH_3$ or $NH_2$, thereby making the product harder to hydrolyze (by action of penicillinase) and otherwise providing desired characteristics not present in the original molecule.

In this connection, the paper of Schwartz et al., op. cit. supra (Background section of this specification), summarizing various papers on inhibition of enzymatic cleavage of polypeptides, should be considered. Schwartz summarizes various papers that teach the addition of appropriate moieties to inhibit hydrolysis and inactivation of products containing the peptide sequence $H_2N$-Tyr-Gly-Gly- . . . —COOH. These papers indicate N-methylating the Tyr residue to inhibit aminopeptidase hydrolysis and cleavage of the Tyr-Gly amide bond. They also indicate amidification, esterification, and replacement with an alcohol of the C-terminal carboxyl. In addition, they indicate similar use of placing a D-aminoacid residue at or toward the C-terminal end or inserting such a group (such as D-Ala or D-Met) between the Tyr and Gly residues. The inventor does not claim to have discovered these expedients, in the context of enkephalins, where they are part of the prior art.

The inventor points out, however, that until the inventor's present discoveries there has been no motivation to apply to the dipeptide YG these teachings concerning enkephalins. There was no motivation because there was no benefit to be gained thereby. In fact, the prior art (which is exemplified by Schwartz, op. cit. supra) has taught that YG is a "biologically inactive" and useless fragment or metabolite of enkephalin; hence, nobody would have a reason to want to prevent enzymatic cleavage of YG in a pharmaceutical product. Only after the present inventor discovered the immunological utility of YG did there exist any motivation to prevent enzymatic cleavage of YG in a pahrmaceutical product.

EXAMPLE 25

Purification of Tyr-D-Ala-Gly

Commercial grade Tyr-D-Ala-Gly (L-tyrosyl-D-alanyl-L-glycine, Sigma Chem. Co., St. Louis, Mo.) was purified in accordance with the procedure of Example 19. The elutant, at approximately 19.0 to 19.2 min, was pure Tyr-D-Ala-Gly, substantially free of contaminants (such as pyrogens and endotoxin.

EXAMPLE 26

DH Assay of Tyr-D-Ala-Gly

The DH assay of Example 21 is repeated with 1:10 serial dilutions of Tyr-D-Ala-Gly of example 25, beginning with 300 fM. The amplifier effect is slightly better than that observed in Table 1 of Gottlieb U.S. Pat. No. 4,699,898. As an additional control, 0.1 ml of 3 fM Tyr-D-Ala-Gly is injected without TT. No reaction is observed over 48 hours.

EXAMPLE 27

Gamma Interferon Assay of Tyr-D-Ala-Gly

The gamma interferon assay of Example 10 was repeated with Tyr-D-Ala-Gly of Example 25. For 1.0 $L_f$/ml TT, the maximum production was approximately 1.5 to 3 times the baseline amount, and the corresponding Tyr-D-Ala-Gly concentration was approximately 20 fM.

The result in Example 27 was a multiplier effect approximately equivalent to that of endogenous YG-material, but at a reagent concentration approximately an order of magnitude lower. That is, Tyr-D-Ala-Gly appears to have been an order of magnitude more potent than endogenous YG-material in this assay. However, the human sources of the materials used were not identical in the two examples. Thus, the observed data suggest, but do not prove, that insertion of D-Ala into synthetic YG increases the potency of the product over that of the endogenous YG product. (Also, the previously described greater potency of the endogenous YG product over the synthetic YG product should be noted, suggesting that insertion of D-Ala into synthetic YG substantially increases the potency of synthetic YG.) The mechanism is attributed to inhibition of enzymatic degradation (hydrolysis) of the active molecule.

EXAMPLE 27A

T-helper Cell Receptor Expression Assay of Tyr-D-Ala-Gly

The T-helper cell receptor expression assay of Example 9 was repeated with Tyr-D-Ala-Gly of Example 25.

The highest figure for high-density of receptors was at approximately 2 fM, and reflected an increase of IL-2 receptors by a factor of approximately 1.5 as a result of Tyr-D-Ala-Gly.

The result in Example 27A was approximately an order of magnitude less in effect than endogenous YGG-material, but it occurred at an apparently lower reagent concentration. Again, however, the two examples cannot strictly be compared because different human materials were used. However, this preliminary data suggests that a slightly greater range of dosage amounts is appropriate for YG expanded by insertion of a D-aminoacid. The inventor considers that the dosage range of $10^{-20}$ moles/kg to 1 fM/kg is appropriate for expanded YG-material.

EXAMPLE 28

Mouse Tests of Tyr-D-Ala-Gly

Ten $BDF_1$ strain mice are divided into two groups of 5. Each mouse is injected with 100 L1210 leukemia cells from ascitic fluid of DBA/2 host mice.

The mice in Group I (control) are thereafter given injections of 0.1 ml sterile saline every third day. The mice in Group II are thereafter given intradermal injections of 2 fg of synthetic Tyr-D-Ala-Gly of Example 25 in 0.1 ml of sterile saline, every third day. The mice were approximately 20 g each, so that 2 fg represents approximately 100 fg/kg of bodyweight.

All of the mice are dead after approximately three weeks. The mean survival rate of the Group II mice is approximately 2.8 days longer than that of the Group I mice.

EXAMPLE 29

DH Assay of Tyr-D-Met-Gly

Tyr-D-Met-Gly is prepared by the method of Coy U.S. Pat. No. 4,127,534, Example 20. It is purified by the procedure of above Example 20, and the DH assay of above Example 26 is carried out, substituting the same molar amounts of the instant product.

Similar results are observed.

EXAMPLE 30

DH Assay of Tyr-D-Thr-Gly

Tyr-D-Thr-Gly is prepared by the method of Coy U.S. Pat. No. 4,127,534, Example 18. It is purified by the procedure of above Example 20, and the DH assay of above Example 26 is carried out, substituting the same molar amounts of the instant product.

Similar results are observed.

EXAMPLE 31

DH Assay of Tyr-D-Leu-Gly

Tyr-D-Leu-Gly is prepared by the method of Coy U.S. Pat. No. 4,127,534, Example 4. It is purified by the procedure of above Example 20, and the DH assay of above Example 26 is carried out, substituting the same molar amounts of the instant product.

Similar results are observed.

EXAMPLE 32

DH Assay of Tyr-D-Ile-Gly

Tyr-D-Ile-Gly is prepared by the method of Coy U.S. Pat. No. 4,127,534, Example 6. It is purified by the procedure of above Example 20, and the DH assay of above Example 26 is carried out, substituting the same molar amounts of the instant product.

Similar results are observed.

EXAMPLE 33

DH Assay of YG Hydrochloride

Commercial grade YG is reacted with HCl to produce YG hydrochloride. The product is purified by the procedure of Example 20, and the DH assay of Example 21 is carried out, substituting the same molar amounts of the instant product as that of YG in Example 21.

Similar results are observed.

EXAMPLE 34

DH Assay of YG Citrate

Commercial grade YG is reacted with citric acid to produce YG citrate. The product is purified by the procedure of Example 20, and the DH assay of Example 21 is carried out, substituting the same molar amounts of the instant product as that of YG in Example 21.

Similar results are observed.

EXAMPLE 35

DH Assay of YG Nitrate

Commercial grade YG is reacted with nitric acid to product YG nitride. The product is purified by the procedure of Example 20, and the DH assay of Example 21 is carried out, substituting the same molar amounts of the instant product as that of YG in Example 21.

Similar results are observed.

EXAMPLE 36

DH Assay of YG Acetate

Commercial grade YG is reacted with acetic acid to produce YG acetate. The product is purified by the procedure of Example 20, and the DH assay of Example 21 is carried out, substituting the same molar amounts of the instant product as that of YG in Example 21.

Similar results are observed.

EXAMPLE 37

DH Assay of Acetylated YG

Commercial grade YG is reacted with acetic anhydride to acetylate the YG, thereby producing n-acetyl tyrosylglycine. The product is purified by the procedure of Example 20, and the DH assay of Example 21 is carried out, substituting the same molar amounts of the instant product as that of YG in Example 21.

Similar results are observed.

EXAMPLE 38

DH Assay of YG Inhibited with Bacitracin 10 ug of synthetic YG of Example 20 are disolved in 50 ul of sterile saline. 100 ug of bacitracin (Aldrich Chem. Co., Milwaukee, Wis., 50,000 units/g) are added and thoroughly mixed.

The DH assay of Example 21 is carried out, using dilutions of the instant mixture containing the same molar amounts of YG as in Example 21.

Similar results are observed. There may be a prolongation of induration.

EXAMPLE 39

DH Assay of YG Inhibited with Puromycin 10 ug of synthetic YG of material 20 are disolved in 50 ml of sterile saline. 100 ug of puromycin dichloride hydrate (Aldrich Chem. Co., Milwaukee, Wis.) are added and thoroughly mixed.

The DH assay of Example 21 is carried out, using dilutions of the instant mixture containing the same molar amounts of YG as in Example 21.

Similar results are observed. There may be a prolongation of induration.

EXAMPLE 40

DH Assay of YG Inhibited with Amastatin 10 ug of synthetic YG of Example 20 are dissolved in 50 ul of sterile saline. 100 ug of synthetic amastatin hydrochloride (Sigma Chemical Co., St. Louis, Mo.) are added and thoroughly mixed.

The DH assay of Example 21 is carried out, using dilutions of the instant mixture containing the same molar amounts of YG as in Example 21.

Similar results are observed. There may be a prolongation of induration.

EXAMPLE 41

DH Assay of N-Methylated YG

Commercial grade YG is reacted with HCHO at pH Similar results are observed. There may be a 6.5 in phosphate buffer reduced with $NaCNBH_4$ to produce N-methylated YG. The product is purified by the procedure of Example 20, and the DH assay of Example 21 is carried out, substituting the same molar amounts of the instant product as that of YG in Example 21.

Similar results are observed. There may be a prolongation of induration.

EXAMPLE 42

DH Assay of C-amidified YG

Commercial grade YG is linked by means of a benzyl ester to a Merrified resin. This is cleaved with $NH_3$ to yield C-amidified YG. The product is purified by the procedure of Example 20, and the DH assay of Example 21 is carried out, substituting the same molar amounts of the instant product as that of YG in Example 21.

Similar results are observed. There may be a prolongation of induration.

EXAMPLE 43

DH Assay of C-esterified YG

Commercial grade YG is reacted with Methanolic-HCL at 56° for 10 minutes to ethyl esterify the C-terminal carboxyl group of the Gly residue. The product is purified by the procedure of Example 20, and the DH assay of Example 21 is carried out, substituting the same molar amounts of the instant product as that of YG in Example 21.

Similar results are observed. There may be a prolongation of induration.

EXAMPLE 44

DH Assay of C-alcoholated YG

Commercial grade YG is bound to a Merrifield resin, and reductively cleaved with lithium borohydride in tetrahydofuran. This process replaces the C-terminal carboxyl group of the Gly residue with ethyl alcohol. The product is purified by the procedure of Example 20, and the DH assay of Example 21 is carried out, substituting the same molar amounts of the instant product as that of YG in Example 21.

Similar results are observed. There may be a prolongation of induration.

An alternative method to deliver YG into the bloodstream or at a site where it can act as a lymphokine, is to administer a related molecule that metabolizes to YG in the body. Schwartz et al., op. cit. supra (Background section of specification), describe how a polypeptide is enzymatically cleaved to moieties, such as Tyr-Gly, that are alleged to be "biologically inactive" or otherwise useless (which they apparently are, for the purposes of Schwartz et al. and those whose work they describe). They describe how injection of Leu- and Met-enkephalin into rats and mice has resulted in the production of, among other things, Tyr-Gly metabolites. They indicate that purified angiotensin-converting enzyme (hereinafter referred to as ACE) and dipeptidylcarboxypeptidase (hereinafter referred to as DPCP) cleave a Gly-Phe amide bond in these polypeptides, producing a Tyr-Gly-Gly moiety; and that the Gly-Gly amide bond is cleaved by dipeptidylaminopeptidase, producing a Tyr-Gly moiety. They also identify ACE as a form of DPCP, and finally conclude that an enzyme designated as "enkephalin-DPCP" or "enkephalinase" is the principal enzyme that metabolizes the polypeptides of interest to them into "biologically inactive" moieties such as Tyr-Gly and Tyr-Gly-Gly. The "biologically inactive" moieties of no interest to Schwartz et al. are products of interest in connection with the instant invention.

It is now within the state of the art to synthesize desired polypeptides by means of an automatic peptide synthesizer, such as the Beckman Model 990. Moreover, as noted in the Background section of the specification, it is known to deliver a therapeutically active molecule by administering another, larger molecule that hydrolyzes, by reason of action of endogenous enzymes, within the body to the desired molecule.

These facts, when considered with the novel information first disclosed in this specification, indicate that a way to deliver YG within the body is to administer Tyr-Gly-A or Tyr-Gly-Gly-B, where A and B represent one or more additional amino acid residues, such as Phe, Phe-Met, Phe-Leu, or a longer amino acid residue sequence. The product so administered must be one susceptible to hydrolysis by one or more endogenous enzymes, for example, as enkephalins are so hydrolyzed. Preferably, the product so administered is not an endogenous enkephalin or endorphin, or other opiate-related product. That is so that possible psychotropic or other physiological effects of such products will be avoided, as well as regulatory and legal problems associated with using designer drugs potentially subject to abuse because of opoid effects.

This method of delivering YG is not at this time considered a preferred embodiment so much as an expedient that a would-be infringer would attempt to avoid the scope of any claims directed solely to Tyr-Gly. Such an expedient might avoid literal infringement, while at the same time appropriating the gist of the invention and the inventor's discoveries and teachings set forth hereinabove. Such expedients are therefore considered within the teaching and scope of the present invention, albeit not the most preferred embodiment.

However, the following caution must be observed in connection with this type of expedient: There is as yet no scientifically valid basis for concluding that a metabolite of a polypeptide is molecularly identical to a smaller peptide having the same amino acid residues, but produced by means of a different procedure. For example, consider the metabolites of Met-enkephalin described by Schwartz et al. (op. cit. supra). Such a metabolite may be identified as having a Tyr-Gly amino acid residue sequence. Yet, there is no clear basis for equating the molecular structure of the metabolite with YG-material endogenously manufactured within the human body. The YG metabolite and the endogenous YG-material may differ in an indefinite number of possible ways: for example, one or the other may be amidified, methylated, acetylated, esterified; different isomeric forms or dimers may be involved; metallic complexes may exist; one may have side chains that the other does not. Whether such difference exist and whether they are clinically important would have to be ascertained, and the necessary technology for doing that may be beyond the present state of the art. Hence, it must be regarded as not scientifically established (and perhaps not possible to establish at this time, given the state of the art) whether a Tyr-Gly metabolite of a polypeptide such as Tyr-Gly-Gly-Phe- . . . (or of any other Tyr-Gly . . . polypeptide) is molecularly identical to endogenous YG-material (Beta-1.11).

EXAMPLE 45

DH Assay of Nonendogenous Polypeptide Susceptible to Enzymatic Hydrolysis

Tyr-Gly-Gly-Phe-Ile is prepared in a Beckman Model 990 automatic peptide synthesizer using conventional techniques. The product is purified by the procedure of Example 20.

The DH assay of Example 21 is carried out, substituting for the YG dilutions of the Example the same molar concentrations of the instant nonendogenous polypeptide. Significant immunological activity is not observed.

The procedure is repeated using serial 10:1 greater concentrations. Activity comparable to that of YG appears to exist at approximately 8–10 orders of magnitude greater molar concentration of polypeptide product than YG in Example 21.

The activity may be attributed to enzymatic cleavage of the Gly-Gly bond by dipeptidylaminopeptidase, producing a Tyr-Gly metabolite. (ACE or enkephalinase cleavage of the Gly-Phe bond to produce Tyr-Gly-Gly is another possibility.)

It is considered that an effective dosage amount in this context must be one that yields approximately the same amount of YG-material in the body as would constitute a correct dosage amount of the latter (i.e., as discussed above after Example 18, approximately from from $3 \times 10^{-18}$ moles to 3 f moles YG/kg).

V. Other Uses of Invention

A. Vaccines

Amplifiers, either singly or in combination, are advantageously used to produce an immune response to weak vaccines. Many pathogens, including several Staphylococcus varieties and fungi responsible for Histoplasmosis or Candidiasis, fail to provoke a strong immune response in certain patients. Moreover, there is no known satisfactory vaccine for conferring immunity on such patients. Such fungal infections are especially dangerous for patients subjected to cancer chemotherapy, or immunosuppressive drugs.

By enhancing the patient's immune response to weak antigens, however, the concurrent administration of the above-described amplifiers, either singly or in combination, provides a means for preparing vaccines against such pathogens. Patients about to receive chemotherapy or transplant surgery are thus advantageously vaccinated prior to treatment, thereby reducing their susceptibility to histoplasmosis or candidiasis. Used as described below, amplifiers expand the scope of available preventive measures in medicine, thereby enlarging the range of weak antigens which can be used for immunization.

EXAMPLE 46

Histoplasmin Vaccine (Beta-1.11)

1 to 10 pg of endogenous YG-material (Beta-1.11 of Example 5) in 100 ul sterile saline is mixed with 100 ul of histoplasmin antigen, U.S.P. (Parke Davis).

The vaccine-amplifier mixture is then administered to the subject (70 kg adult person) by standard procedures, thereby immunizing the subject against histoplasmin pathogen.

EXAMPLE 46A

Malaria Vaccine (Beta-1.11)

1 to 10 pg of endogenous YG-material (Beta-1.11 of Example 5) in 100 ul sterile saline is injected intradermally into a 70 kg adult person (the subject). Concurrently the physician administers malaria vaccine by standard procedures, thereby immunizing the subject.

EXAMPLE 46B

American Trypanosomiasis Vaccine (Beta-1.11)

1 to 10 g of endogenous YG-material (Beta-1.11 of Example 5) in 100 ul sterile saline is injected intradermally into a 70 kg adult person (the subject). Concurrently the physician administers American trypanpsomiasis vaccine by standard procedures, thereby immunizing the subject.

EXAMPLE 46C

Leishmaniasis Vaccine (Beta-1.11)

1 to 10 g of endogenous YG-material (Beta-1.11 of Example 5) in 100 ul sterile saline is injected intradermally into a 70 kg adult person (the subject). Concurrently the physician administers leishmaniasis vaccine by standard procedures, thereby immunizing the subject.

EXAMPLE 47

Histoplasmin Vaccine (Synthetic YG)

5 to 50 pg of synthetic YG of Example 20 in 100 ul sterile saline is mixed with 100 ul of histoplasmin antigen, U.S.P. (Parke Davis).

The vaccine is then administered to the subject (70 kg person) by standard procedures, thereby immunizing the subject against the pathogen.

EXAMPLE 47A

Malaria Vaccine (Synthetic YG)

5 to 50 pg of synthetic YG of Example 20 in 100 ul sterile saline is injected intradermally into a 70 kg adult person (the subject). Concurrently the physician administers malaria vaccine by standard procedures, thereby immunizing the subject.

EXAMPLE 47B

American Trypanosomiasis Vaccine (Synthetic YG)

5 to 50 pg of synthetic YG of Example 20 in 100 ul sterile saline is injected intradermally into a 70 kg adult person (the subject). Concurrently the physician administers American trypanosomiasis vaccine by standard procedures, thereby immunizing the subject.

EXAMPLE 47C

Leishmaniasis Vaccine (Synthetic YG)

5 to 50 pg of synthetic YG of Example 20 in 100 ul sterile saline is injected intradermally into a 70 kg adult person (the subject). Concurrently the physician administers leishmaniasis vaccine by standard procedures, thereby immunizing the subject.

EXAMPLE 47D

Pseudorabies Vaccine (Synthetic YG)

15 to 150 pg of synthetic YG of Example 20 in 100 l sterile saline is injected intradermally into a 600-pound hog. Concurrently the veterinarian administers psuedoabies pathogen by standard procedures, thereby immunizing the hog.

Chemically linking the antigen to the amplifier is an alternative to merely mixing the two products together, to assure appropriate receptor site stimulation. Appropriate means of chemical linkage include a complex, a covalent bond, an ionic bond, or a hydrogen bond.

The use of endogenous YG-material and synthetic YG above is considered to be merely illustrative. It is considered that similar results are obtained by repeating Examples 46–46C with Beta-1.12 (endogenous YGG-material), Beta-1.13, or Zeta-2, and by repeating Examples 47–47D with synthetic YGG or the products of Examples 25 to 44.

B. Diagnostics

Amplifier materials accelerate the onset of DH reaction to antigen. Use of amplifier therefore provides a means for furnishing a more rapid diagnostic test for determining whether a subject has been exposed to a given pathogen or other antigen. For example, a more rapid test for exposure to tuberculosis is now considered desirable, since it presently requires 24 to 36 hours to obtain a result. That length of time requires that the test subject return to the clinic for a second visit, causing expense and inconvenience to him or her, or else the subject must mail in a post card (which may be inaccurate or unreliable).

EXAMPLE 48

Accelerated TB test

Patient A is known to test positive to tuberculin. Patient B is known to test negative.

Preparation C is prepared, consisting of 0.5 tuberculin units of Purified Protein Derivatives (Parke Davis, TUBERCULIN-APLISOL, PPD) in 0.2 ml saline. Preparation D is prepared by combining 0.1 ml of Preparation C with 0.1 ml of saline containing approximately 10 fg of endogenous YG-material (Beta-1.11 of Example 5).

Patients A and B are each injected intradermally at two sites with 0.1 ml of Preparation C and 0.1 ml of Preparation D, respectively. The following dermal reactions (mm × mm) are observed with respect to Preparations C and D, respectively:

|       | Patient A |         | Patient B |   |
|-------|-----------|---------|-----------|---|
| Hours | C         | D       | C         | D |
| 5     | 0         | 18 × 20 | 0         | 0 |
| 8     | 0         | 16 × 18 | 0         | 0 |
| 24    | 18 × 20   | 16 × 18 | 0         | 0 |
| 36    | 16 × 18   | 10 × 12 | 0         | 0 |

Patient A is observed to display a positive teat within 5 to 8 hours where amplifier is used, as compared with 24 hours where amplifier is not used. Control patient B displays no response to PPD with or without amplifier.

EXAMPLE 49

Accelerated Histoplasmosis test

Patient A is known to test positive to histoplasmin. Patient B is known to test negative.

Preparation C is prepared, consisting of 0.05 ml of histoplasmin antigen, U.S.P. (Parke Davis, 1:100 dilution) in 0.2 ml saline. Preparation D is prepared by combining 0.1 ml of Preparation C with 0.05 ml of saline containing approximately 10 fg of synthetic YG of Example 20.

Patients A and B are each injected intradermally at two sites with 0.1 ml of Preparation C and 0.1 ml of Preparation D, respectively. The following dermal reactions (mm × mm) are observed with respect to Preparations C and D, respectively:

|       | Patient A |         | Patient B |   |
|-------|-----------|---------|-----------|---|
| Hours | C         | D       | C         | D |
| 5     | 0         | 18 × 20 | 0         | 0 |
| 8     | 0         | 16 × 18 | 0         | 0 |
| 24    | 18 × 20   | 16 × 18 | 0         | 0 |
| 36    | 16 × 18   | 10 × 12 | 0         | 0 |

The same procedure is appropriate for any other antigen-based diagnostic test utilizing a recall antigen that causes a DH response. Further, the use of endogenous YG-material and synthetic YG above is considered to be merely illustrative. It is considered that similar results are obtained by repeating Examples 48 and 49 with Beta-1.12 (endogenous YGG-material), Beta-1.13, Zeta-2, synthetic YGG, or the products of Examples 25 to 44.

GENERAL CONCLUDING REMARKS

The above described endogenous amplifiers of the immune system are considered to be materials whose natural function is regulation of the immune response, directly with respect to cell-mediated immunity and perhaps indirectly affecting humoral immunity as well. The materials have been prepared with a high degree of purity such that their molecular structure has been more fully characterized than higherto possible. Furthermore, the materials of this invention have been purified sufficiently to permit their administration to human subjects to produce beneficial effects, without known harmful side effects. Such beneficial effects include immunostimulation of immunodeficient patients, such as victims of AIDS and ARC, and retardation of the normal progression to AIDS from ARC. While not curvative of AIDS and ARC, the materials of the invention have substantial therapeutic effects, alleviating certain AIDS/ARC symptoms and reversing or slowing some harmful effects of the diseases. For example, candidiasis has been shown in the above data to be alleviated by this treatment. In addition, synthetic products have been described with molecular structures based on that of the endogenous materials, and possessing similar immunological utility.

The products described above have been shown to increase a person's endogenous production of various modifiers of biological responses that human lymphocytes produce, at least when the person's immune system has not already been so injured as to be beyond the reach of therapy. Such leukocyte-generated modifiers of biological response have been shown to include the specific lymphokines IL-2 and gamma-interferon.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains.

As the preceding examples and discussion show, the invention can be practiced with a genus of products characterized by the presence of Tyr and Gly amino acid residues, with optional admixture with other products and with optional modification of certain parts of the structure. As lexicographer for his claims, the applicant defines the following terms used in the claims to have the following meanings:

"YG Product" means YG; methylated, acetylated, amidified, esterified, or alcoholated YG; or a pharmaceutically acceptable salt of any of the foregoing.

"Inhibited YG Product" means a YG Product mixed with bacitracin, puromycin, amastatin, or another means for inhibiting enzymatic hydrolysis of a Tyr-Gly bond.

"Expanded YG Product" means Tyr-X-Gly, where X is a D-aminoacid; said Tyr-X-Gly methylated, acetaylated, amidified, esterified, or alcoholated; or a pharmaceutically acceptable salt of any of the foregoing.

"YGG Product" means YGG: methylated, acetylated, amidified, esterified, or alcoholated YGG; or a pharmaceutically acceptable salt of any of the foregoing.

The subject matter claimed is:

1. A pharmaceutical composition comprising a pharmaceutically acceptable inert carrier and an effective dosage amount of YG Product, essentially free of endotoxin and pyrogen.

2. A packaged pharmaceutical composition according to claim 1 wherein said YG product is endogenous YG-product.

3. A pharmaceutical composition according to claim 1 wherein said YG product is endogenous YG-product.

4. A composition according to claim 1 wherein said YG product is synthetic.

5. A composition according to claim 1 wherein said YG product is mixed with YGG product, and said YG product and said YGG product are respectively present in relative proportions (w/w) of from 10:1 to 25:1.

6. A composition according to claim 1 wherein phenylalanine is also included.

7. A composition according to claim 6 wherein at least one of the following is also included: Phe-Ser, Gly-Gly, Gly-Glu.

8. A composition according to claim 4 wherein said synthetic YG product is N-methylated.

9. A composition according to claim 4 wherein said synthetic YG product is synthetic YG product whose C-terminal carboxyl group is amidified, esterified, or replaced with a pharmaceutically acceptable alcohol.

10. A composition according to claim 1 wherein an effective dosage amount of diagnostic antigen is also included.

11. The composition of claim 10 wherein said antigen is tuberculin.

12. A composition according to claim 1 wherein a dosage amount of an antigen or pathogen associated with a disease is also included and:
    (a) said disease-associated antigen or pathogen ordinarily does not provide more than a negligible cell-mediated immune-system response when a person's immune system is challenged with injection of said antigen or pathogen in vaccine form; and
    (b) said dosage amount of YG product is effective to provoke a cell-mediated immune-system response when a person's immune system is challenged with said antigen or pathogen in vaccine form in the presence of said dosage amount of amplifier.

13. A composition according to claim 12 wherein said antigen or pathogen is for histoplasmosis, malaria, American trypanosomiasis, leishmaniasis, or pseudorabies.

14. A pharmaceutical composition comprising a pharmaceutically acceptable inert carrier and an effective dosage amount of inhibited YG product.

15. A composition according to claim 14 wherein said YG product is inhibited by mixture with bacitracin, puromycin, or amastatin.

16. A pharmaceutical composition comprising a pharmaceutically acceptable inert carrier and an effective dosage amount of expanded YG product.

17. A composition according to claim 16 wherein said amount is more than $3 \times 10^{-19}$ mole per dosage unit and less than 3 f mole per dosage unit.

18. A composition according to claim 16 wherein said expanded YG product is Tyr-D-Ala-Gly and said amount is more than 1 fg per dosage unit and is less than 1 pg per dosage unit.

19. A pharmaceutical composition comprising a pharmaceutically acceptable inert carrier and a predetermined amount of an artificial polypeptide, said polypeptide being one which metabolizes to YG as a result of the action of at least one endogenous human enzyme, and said predetermined amount being sufficient to provide said YG in an effective dosage amount.

20. A composition according to claim 19 wherein said dosage amount is one effective to increase human immune responsiveness to recall antigen.

21. A pharmaceutical composition comprising an amount of Tyr-gly dissolved or suspended in a pharmaceutically acceptable carrier suitable for injection, said amount being effective for stimulating the human immune system and said composition being substantially free of pyrogens and endotoxins.

22. A composition according to claim 21 wherein said carrier is sterile saline.

23. A composition according to claim 22 wherein said carrier is sterile water.

24. A pharmaceutical composition comprising Tyr-Gly, essentially free of endotoxin and pyrogen, and a pharmaceutically acceptable carrier.

25. A pharmaceutical composition comprising an amount of Beta-1.13 that is effective for stimulating the human immune system, and dissolved or suspended in a pharmaceutically acceptable carrier suitable for injection, said composition being substantially free of pyrogen and endotoxin.

26. A pharmaceutical composition comprising an amount of at lest one of the following amplifiers—Beta-1.0, Beta-1.1, Beta-1.11, Beta-1.13—dissolved or suspended in a pharmaceutically acceptable carrier suitable for injection, wherein said amount of amplifier is effective for stimulating the human immune system and wherein said composition is substantially free of pyrogen and endotoxin.

27. A composition according to claim 26 wherein phenylalanine is also present.

28. In a vaccinal composition comprising a carrier and a vaccine-dosage amount of a disease-associated antigen or pathogen known not to provoke more than a negligible cell-mediated immune-system response when a person's immune system is challenged therewith, the improvement consisting of: a YG-dosage amount of YG product mixed with, or chemically linked to, said antigen or pathogen, said YG-dosage amount being sufficient to provoke more than a negligible cell-mediated immune-system response when a persons's immune system is challenged with said vaccine-dosage amount of antigen or pathogen in the presence of said YG-dosage amount of YG-material.

* * * * *